United States Patent
Cervenakova et al.

(10) Patent No.: US 9,051,390 B2
(45) Date of Patent: Jun. 9, 2015

(54) INHIBITION OF PRION PROPAGATION BY RECEPTOR ASSOCIATED PROTEIN (RAP), ITS DERIVATIVES, MIMETICS AND SYNTHETIC PEPTIDES

(75) Inventors: Larisa Cervenakova, Rockville, MD (US); Oksana Yakovleva, Derwood, MD (US)

(73) Assignee: American National Red Cross, Washington, DC (US)

( * ) Notice: Subject to any disclaimer, the term of this patent is extended or adjusted under 35 U.S.C. 154(b) by 107 days.

(21) Appl. No.: 13/265,242

(22) PCT Filed: May 17, 2010

(86) PCT No.: PCT/US2010/001455
§ 371 (c)(1), (2), (4) Date: Jan. 19, 2012

(87) PCT Pub. No.: WO2010/134970
PCT Pub. Date: Nov. 25, 2010

(65) Prior Publication Data
US 2012/0135936 A1    May 31, 2012

Related U.S. Application Data

(60) Provisional application No. 61/180,406, filed on May 21, 2009, provisional application No. 61/218,752, filed on Jun. 19, 2009.

(51) Int. Cl.
C07K 14/705    (2006.01)
A61K 38/17    (2006.01)

(52) U.S. Cl.
CPC ........... *C07K 14/705* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 2004/0110938 A1 * | 6/2004 | Parekh et al. | 536/23.5 |
| 2005/0042227 A1 | 2/2005 | Zankel et al. | |
| 2008/0268474 A1 | 10/2008 | Hammond et al. | |

FOREIGN PATENT DOCUMENTS

| | | |
|---|---|---|
| JP | 2007-526227 | 9/2007 |
| WO | WO 2005/002515 A2 | 1/2005 |

OTHER PUBLICATIONS

Tsuboi et al. 2009 "Continuous intraventricular infusion of pentosan polysulfate: clinical trial against prion diseases" Neuropathology 29(5):632-6 (abstract only).*
Horwich and Weissman 1997 "Deadly Conformations—Protein Misfolding in Prion disease" cell 89:499-510.*
Herz et al. 1991 "39-kDa protein modulates binding of ligands to low density lipoprotein receptor-related protein/alpha2-macroglobulin receptor" JBC 266(31):21232-21238.*
Akimov et al., "Persistent propagation of variant Creutzfeldt-Jakob disease agent in murine spleen stromal cell culture with features of mesenchymal stein cells," J Virol., 2008, vol. 82, pp. 10959-10962, Epub., Aug. 20, 2008, American Society for Microbiology.
Akimov et al.,"Murine bone marrow stromal cell culture with features of mesenchymal stem cells susceptible to mouse-adapted human TSE agent, Fukuoka-1," Folia Neuropathol. 2009, vol. 47, pp. 205-214.
Ashcom et al., "The human alpha 2-macroglobulin receptor: identification of a 420-kD cell surface glycoprotein specific for the activated conformation of alpha 2-macroglobulin," J. Cell. Biol., 1990, vol. 110, pp. 1041-1048, The Rockefeller University Press.
Caughey et al., "Prions and their partners in crime," Nature, 2006, vol. 443, pp. 803-810, Review, Nature Publishing Group.
Caughey et al., "Prions and transmissible spongiform encephalopathy (TSE) chemotherapeutics: A common mechanism for anti-TSE compounds?" Acc Chem Res., 2006, vol. 39, No. 9, pp. 646-653, American Chemical Society.
Edenhofer et al., "Prion protein PrPc interacts with molecular chaperones of the Hsp60 family," J Virol., 1996, vol. 70, No. 7, pp. 4724-4728, American Society for Microbiology.
Ellis et al., "Plasminogen activation is stimulated by prion protein and regulated in a copper-dependent manner," Biochemistry, 2002, vol. 41, pp. 6891-6896, American Chemical Society.
Furukawa et al., "A heparin binding protein whose expression increases during differentiation of embryonal carcinoma cells to parietal endoderm cells: cDNA cloning and sequence analysis," J. Biochem., 1990, vol. 108, No. 2, pp. 297-302.
Gauczynski et al., "The 37-kDa/67-kDa laminin receptor acts as the cell-surface receptor for the cellular prion protein," EMBO J., 2001, vol. 20, pp. 5863-5875, European Molecular Biology Organization.
Haley et al., "Detection of CWD prions in urine and saliva of deer by transgenic mouse bioassay," PLoS One, 2009, vol. 4, Issue 3, p. 4848, Epub., Mar. 18, 2009.
Herz et al., "39-kDa protein modulates binding of ligands to low density lipoprotein receptor-related protein/alpha 2-macroglobulin receptor," J. Biol. Chem., 1991, vol. 266, No. 31, Issue of Nov. 5, pp. 21232-21238, The American Society for Biochemistry and Molecular Biology, Inc.
Horonchik et al., "Heparan sulfate is a cellular receptor for purified infectious prions," J Biol Chem., 2005, vol. 280, p. 17062, Epub., Published, JBC Papers in Press, Jan. 24, 2005.
Hsiao et al., "Spontaneous neurodegeneration in transgenic mice with prion protein codon 101 proline—leucine substitution," Ann N Y Acad Sci., 1991, vol. 640 pp. 166-170.
Kerr et al., "Inhibition of Aβ aggregation and neurotoxicity by the 39-kDa receptor-associated protein", J Neurochem. 2010 vol. 112:1199-209. Epub Dec. 10, 2009, International Society for Neurochemistry.
Korenberg et al., "Chromosomal localization of human genes for the LDL receptor family member glycoprotein 330 (LRP2) and its associated protein RAP (LRPAP1)". Genomics 1994, vol. 22, pp. 88-93, Academic Press, Inc.

(Continued)

*Primary Examiner* — Gregory S Emch
*Assistant Examiner* — Adam M Weidner
(74) *Attorney, Agent, or Firm* — RatnerPrestia

(57) ABSTRACT

A pharmaceutical formulation and method of treatment of prion disease include a RAP agent with a pharmaceutically acceptable carrier and/or excipient, and the administration of same to a subject suffering from or at risk of a prion disease. The RAP agent is an effective means for the prevention and/or treatment of various prion diseases regardless whether the disease is acquired by infection or by genetic mutation.

12 Claims, 9 Drawing Sheets

(56) References Cited

OTHER PUBLICATIONS

Kornblatt et al., "The fate of the prion protein in the prion/plasminogen complex," Biochem Biophys Res Commun., 2003, vol. 305, pp. 518-522, Elsevier Science (USA).
Liao et al. "Human prion protein cDNA: molecular cloning, chromosomal mapping, and biological implications," Science, 1986, vol. 233, pp. 364-367.
Pan et al., "Efficient transfer of receptor-associated protein (RAP) across the blood-brain barrier," J Cell Sci., 2004, vol. 117(Pt 21), pp. 5071-5078, Epub., Sep. 21, 2004, The Company of Biologists.
Pankiewicz et al., "Clearance and prevention of prion infection in cell culture by anti-PrP antibodies," Eur J Neurosci., 2006, vol. 23, No. 10, pp. 2635-2647.
Parkyn et al., "LRP1 controls biosynthetic and endocytic trafficking of neuronal prion protein," J Cell Sci., 2008, vol. 121(Pt 6), pp. 773-783, Epub., Feb. 19, 2008, The Company of Biologists.
Praus et al., "Stimulation of plasminogen activation by recombinant cellular prion protein is conserved in the NH2-terminal fragment PrP23-110," Thromb., 2003, vol. 89, pp. 812-819 2003, Schattauer GmbH, StuttgartHaemost.
Rieger et al., "The human 37-kDa laminin receptor precursor interacts with the prion protein in eukaryotic cells," Nat Med., 1997, vol. 3, No. 12, pp. 1383-1388.
Rudd et al., "Prion glycoprotein: structure, dynamics, and roles for the sugars," Biochemistry, 2001, vol. 40, No. 13, pp. 3759-3766, American Chemical Society.
Santuccione et al., "Prion protein recruits its neuronal receptor NCAM to lipid rafts to activate p59fyn and to enhance neurite outgrowth," J Cell Biol., 2005, vol. 169, pp. 341-354, The Rockefeller University Press.
Saunders et al., "Prions in the environment: occurrence, fate and mitigation" Prion. 2008 vol. 2:4, 162-9. Epub Oct. 26, 2008. Review, Landes Bioscience.
Stahl et al., "Scrapie Prion Protein contains a Phosphatidylinositol Glycolipid", Cell, 1987, vol. 51, pp. 229-240, Cell Press.
Stahl et al., "Prions and prion proteins," FASEB J., 1991, vol. 5, pp. 2799-2807.
Strickland et al., "Primary structure of alpha 2-macroglobulin receptor-associated protein. Human homologue of a Heymann nephritis antigen," J Biol Chem., 1991, vol. 266, No. 20, pp. 13364-13369, The Journal of Biological Chemistry.
Taylor et al., "Role of lipid rafts in the processing of the pathogenic prion and Alzheimer's amyloid-beta proteins," Seminars in Cell & Dev Biol., 2007, vol. 18, pp. 638-648, Epub., Jul. 24, 2007, Review, Elsevier Ltd.
Telling et al., "Prion propagation in mice expressing human and chimeric PrP transgenes implicates the interaction of cellular PrP with another protein," Cell, 1995, vol. 83, pp. 79-90, Cell Press.
Will et al., "A new variant of Creutzfeldt-Jakob disease in the UK," Lancet, 1996, vol. 347, pp. 921-925.
Williams et al., "A novel mechanism for controlling the activity of alpha 2-macroglobulin receptor/low density lipoprotein receptor-related protein. Multiple regulatory sites for 39-kDa receptor-associated protein," J. Biol Chem., 1992, vol. 267, No. 13, pp. 9035-9040, The American Society for Biochemistry and Molecular Biology, Inc.
Willnow, "Receptor-associated protein (RAP): a specialized chaperone for endocytic receptors," Biol Chem., 1998, vol. 379, pp. 1025-1031.
Xu et al. "Receptor-associated protein (RAP) plays a central role in modulating Abeta deposition in APP/PS 1 transgenic mice," PLoS One, 2008, vol. 3, Issue 9, p. 3159.
Zomosa-Signoret et al., *Physiological role of the cellular prion protein*. Vet Res. 2008, vol. 39:9. Epub., Nov. 27, 2007. Review.
Zhang et al., "Prion protein is expressed on long-term repopulating hematopoietic stem cells and is important for their self-renewal," Proc Natl Acad Sci, U S A, 2006, vol. 103, No. 7, pp. 2184-2189, Epub., Feb. 2006.
Zanata et al., "Stress-inducible protein 1 is a cell surface ligand for cellular prion that triggers neuroprotection," EMBO J., 2002, vol. 21, No. 13, pp. 3307-3316.

Supplementary European Search Report, EP 10 77 8035, Dec. 3, 2012.
Database UniProt [Online], Dec. 21, 2004, "SubName: Full=Putative uncharacterized protein DKFZp45912430;", XP002687467, retrieved from EBI accession No. UniProt:Q5RD62, Database accession No. Q5RD62 *sequence*.
Database UniProt [Online], Jul. 5, 2004, "SubName: Full=Lrpap1 protein; Flags: Fragment;", XP002687468, retrieved from EBI accession No. UniProt:Q6PEM5, Database accession No. Q6PEM5 *sequence*.
Database Geneseq [Online], Jan. 29, 2004, "Rat Protein Q99068, SEQ ID No. 10388.", XP002687469, retrieved from EBI accession No. GSP: ADD44957, Database accession No. ADD44957 *sequence*.
Database UniProt [Online], Jun. 1, 1998, "SubName: Full=Receptor-associated protein; Flags: Precursor;", XP002687470, retrieved from EBI accession No. UniProt: 057378, Database accession No. 057378 *sequence*.
Database UniProt [Online], Oct. 1, 2003, "SubName: Full=LOC398643 protein; Flags: Fragment;", XP002687471, retrieved from EBI accession No. UniProt:Q7SYR7, Database accession No. Q7SYR7 *sequence*.
Database UniProt [Online], Jun. 1, 2003, "SubName: Full=Low density lipoprotein receptor-related protein associated protein 1; LQWKKLKAEG MDEDGEREAK LRRNFNIILA KYGMDGKKDT RTLDSNRLKD HEVKIGDTFD", XP002687472, retrieved from EBI accession No. UniProt: Q7ZW96, Database accession No. Q7ZW96 *sequence*.
Hooper Nigel M. et al: "Mechanism of the metal-mediated endocytosis of the prion protein," Biochemical Society Transactions, vol. 36, No. Part 6, Dec. 2008, pp. 1272-1276, XP009164829, ISSN: 0300-5127, University of Leeds, Leeds, U.K.
David R. Taylor et al: "The low-density lipoprotein receptor-related protein 1 (LRP1) mediates the endocytosis of the cellular prion protein," Biochemical Journal, vol. 402, No. 1, Feb. 2007, pp. 17-23, XP055044607, ISSN: 0264-6021, DOI: 10.1042/BJ20061736, Biochemical Society, Great Britain.
Parkyn Celia J. et al: "LRPJ controls biosynthetics and endocyctic trafficking of neuronal prion protein," Journal of Cell Science, vol. 121, No. 6, Mar. 2008, pp. 773-783, XP002687473, ISSN: 0021-9533, The Company of Biologists, 2008.
Jen Angela et al: "Neuronal low-density lipoprotein receptor-related protein 1 binds and endocytoses prion fibrils via receptor cluster 4," Journal of Cell Science, vol. 123, No. 2, Jan. 2010, pp. 246-255, XP002687474, ISSN: 0021-9533.
Cervenakova Larisa et al: "Receptor-associated Protein (RAP) Inhibits Generation of Disease-associated Prion Protein (PrPd) in Cell Cultures," Prion, vol. 4, No. 3, Jul. 2010, pp. 205-206, XP009164842, & International Prion Congress, Salzsburg, Austria, Sep. 8-11, 2010.
International Search Report (PCT/ISA/210) issued on Sep. 7, 2010, by Japanese Patent Office as the International Searching Authority for International Application No. PCT/US2010/001455.
Leucht, C., et al., "The 37kDa/67 kDa Laminin Receptor is Required for PrP$^{sc}$ Propagation in Scrapie-Infected Neuronal Cells," Scientific Report, EMBO Reports, vol. 4, No. 3, 2003, pp. 290-295.
European Examination Report dated Nov. 11, 2014 in European Application No. 10 778 035.5.
Palomares et al., Production of Recombinant Proteins, in *Methods in Molecular Biology*, vol. 267: *Recombinant Gene Expression: Reviews and Protocols*, Second Edition (P. Balbás and A. Lorence eds., Humana Press Inc.) pp. 15-51 (2004).
Borchelt et al., J Biol Chem., 267:16188-99 (1992).
Brandner et al., Nature, 379(6563):339-43 (1996).
Bu et al., EMBO J., 14:2269-80 (1995).
Caughey and Raymond, J Biol Chem., 266:18217-23 (1991).
Caughey et al., J Virol., 65:6597-603 (1991).
Gauczynski et al., EMBO J., 20(21):5863-75 (2001).
Gauczynski et al., J Infect Dis., 194:702-9. (2006).
Horonchik et al., J. Biol. Chem., 280:17062-67 (2005).
Hundt et al., EMBO J., 20:5876-86 (2001).
Jen et al., J Cell Sci., 123(Pt 2):246-55 (2010).
Kurasawa et al., Biochemistry, 54:481-9 (2015).
Lazic et al., Biochemistry, 42:14913-20 (2003).

(56) References Cited

OTHER PUBLICATIONS

Magalhães et al., J Neurosci., 25:5207-16 (2005).
McKinley et al., Lab Invest., 65:622-30 (1991).
Migliorini et al., J Biol Chem, 278:17986-17992 (2003).
Neels et al., J Biol Chem, 274:31305-11 (1999).
Obermoeller et al., J Biol Chem, 272:10761-68 (1997).
Orr et al., J Cell Biol, 161:1179-89 (2003).
Parkyn et al., J Cell Sci, 121(6):773-83 (2008).
Pflanz et al., J Mol Biol., 388:721-9. (2009).
Rouvinski et al., J Cell Biol., 204(3):423-41 (2014).
Sarafanov et al., Thromb Haemost., 98:1170-81 (2007).
Willnow and Herz, J Cell Sci, 107:719-26, (1994).

* cited by examiner

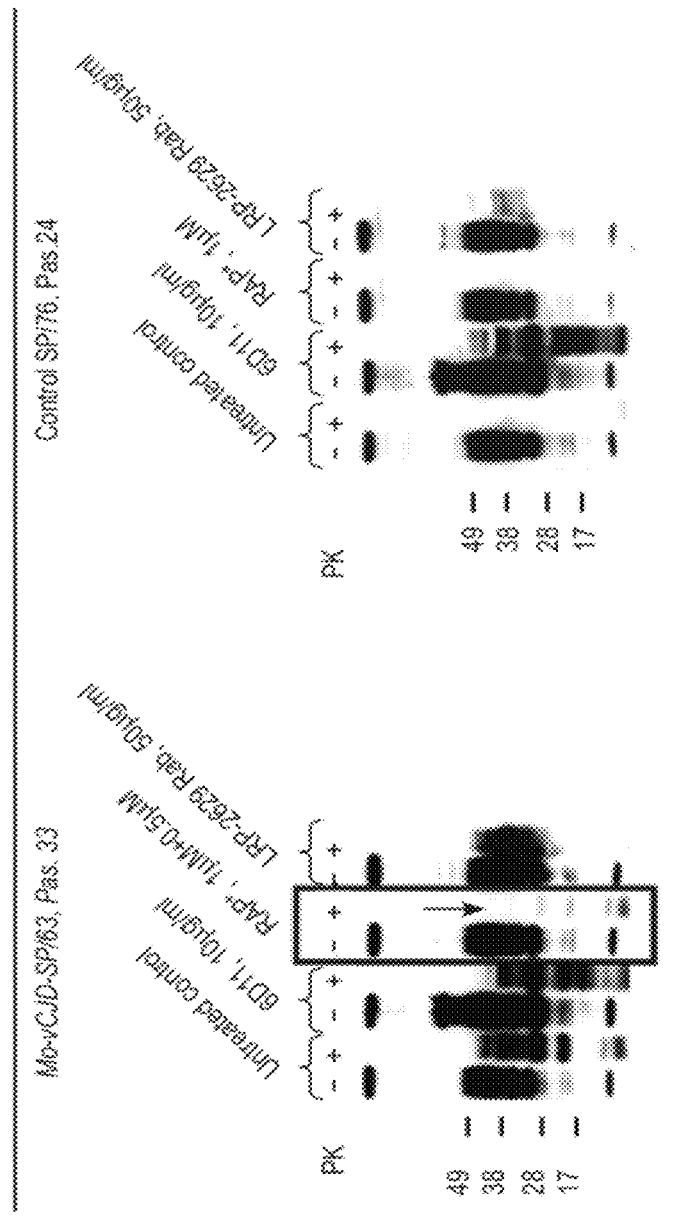

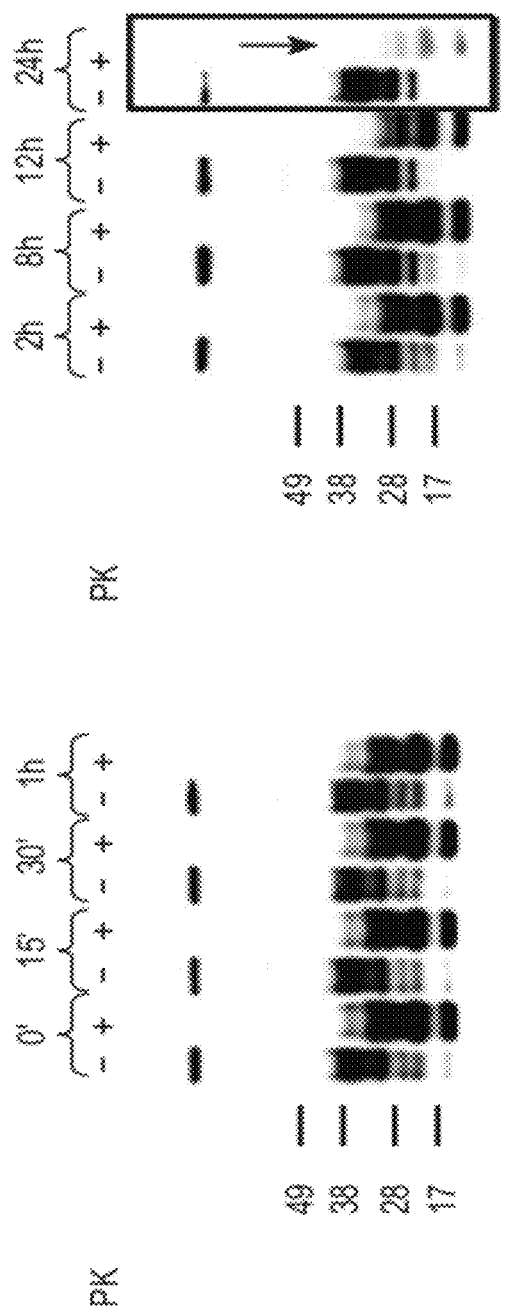

Effect of RAP on PrPress formation in mo-vCJD-SP/63 cell line infected with mouse-vCJD: Dose-dependent inhibition
- Proteins were concentrated by Methanol precipitation.
- (-) and (+) Proteinase K (PK)- treated samples represent total PrP and pathologic PrPress, respectively.
- Anti-PrP monoclonal antibody 6D11 diluted 1:10,000.
- Inhibition of PrPres formation by RAP is shown by arrows.

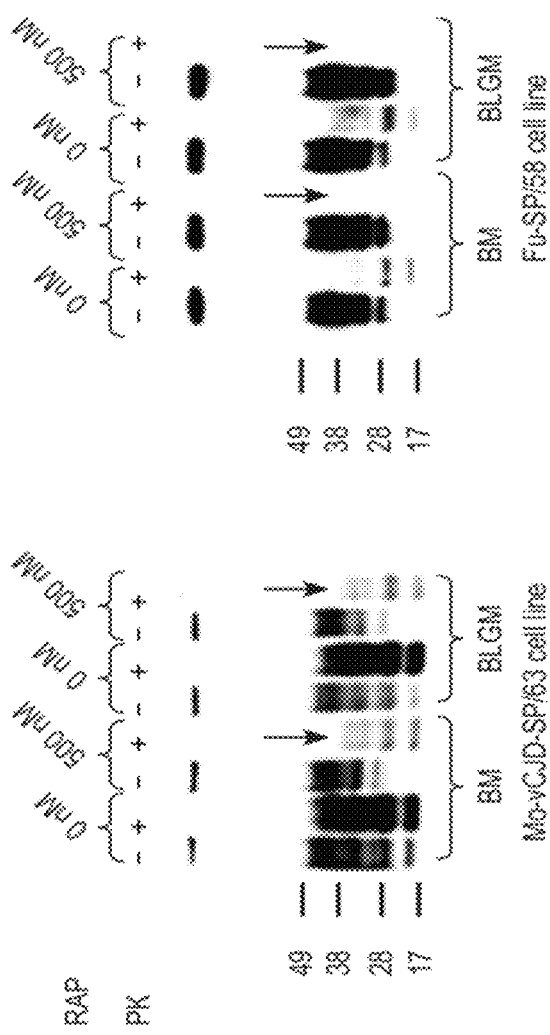

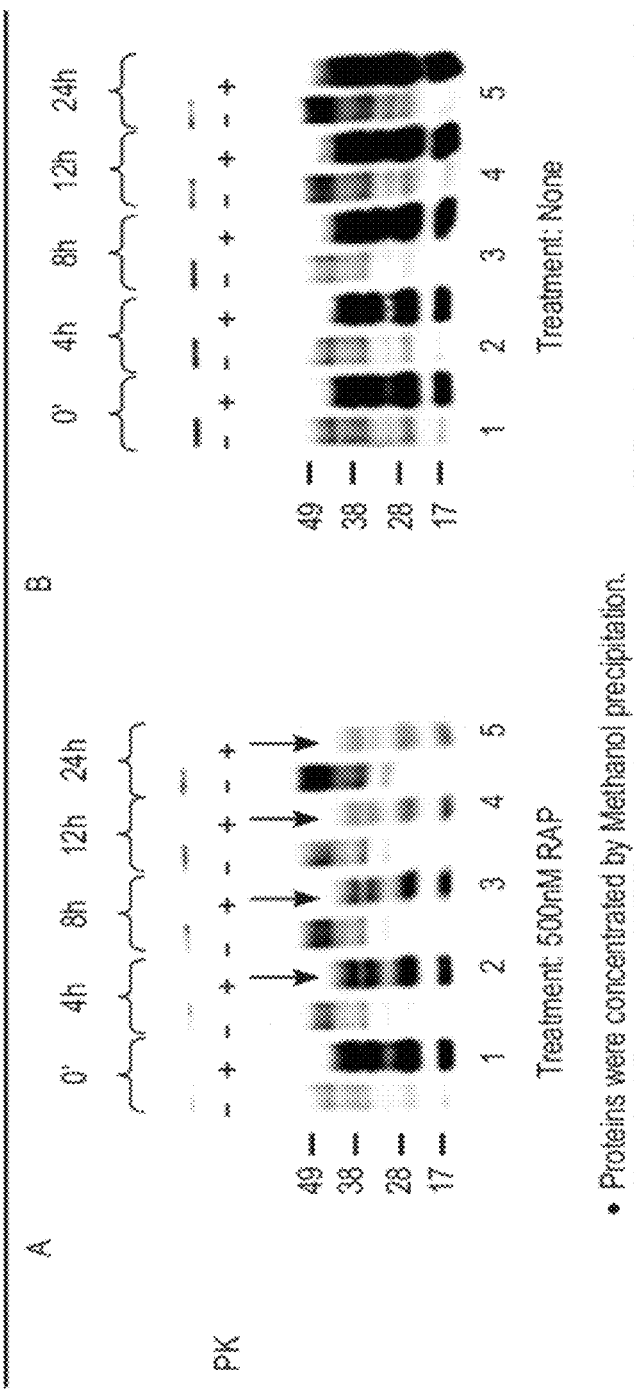

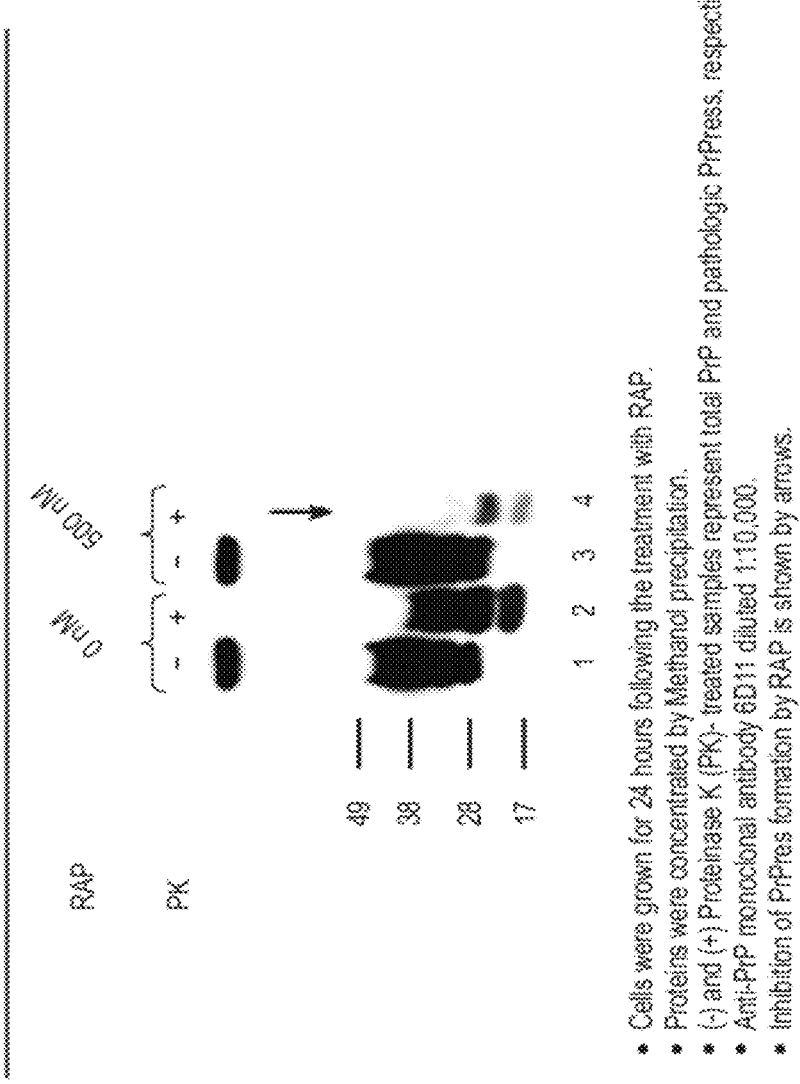

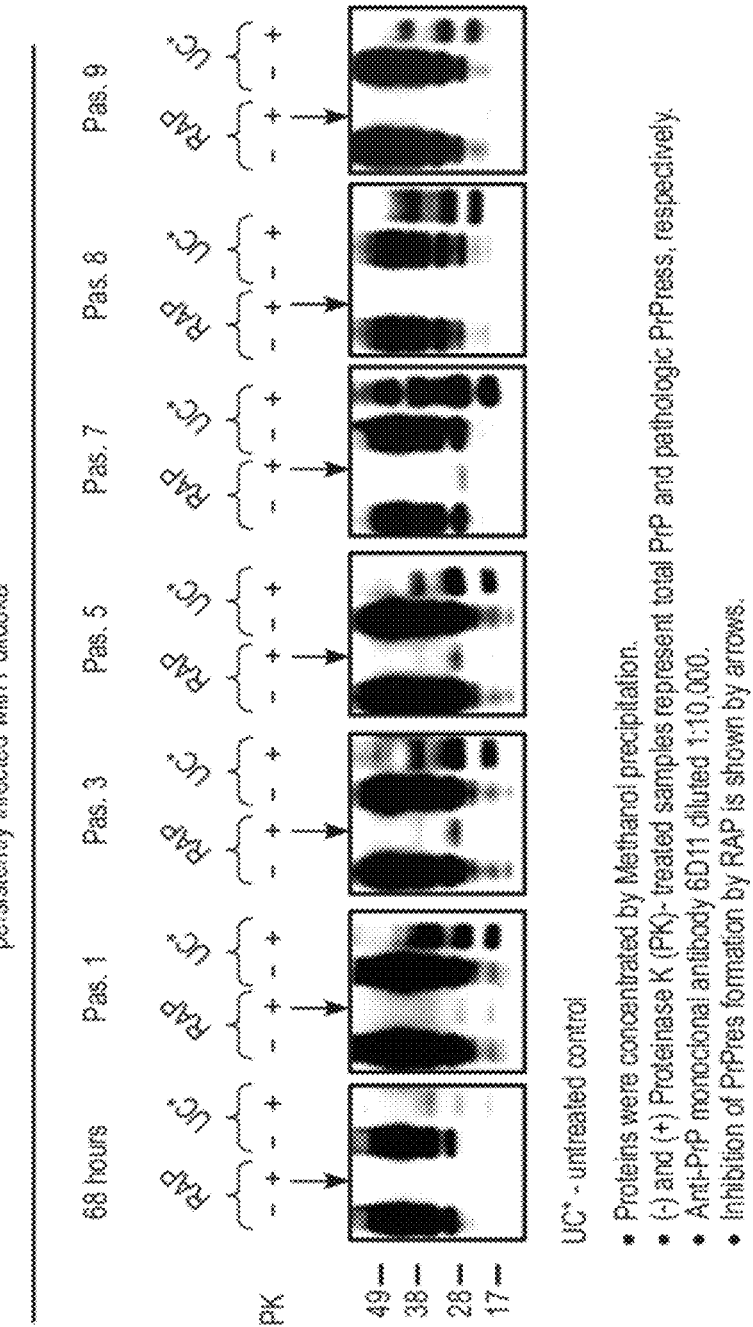

Figure 8:
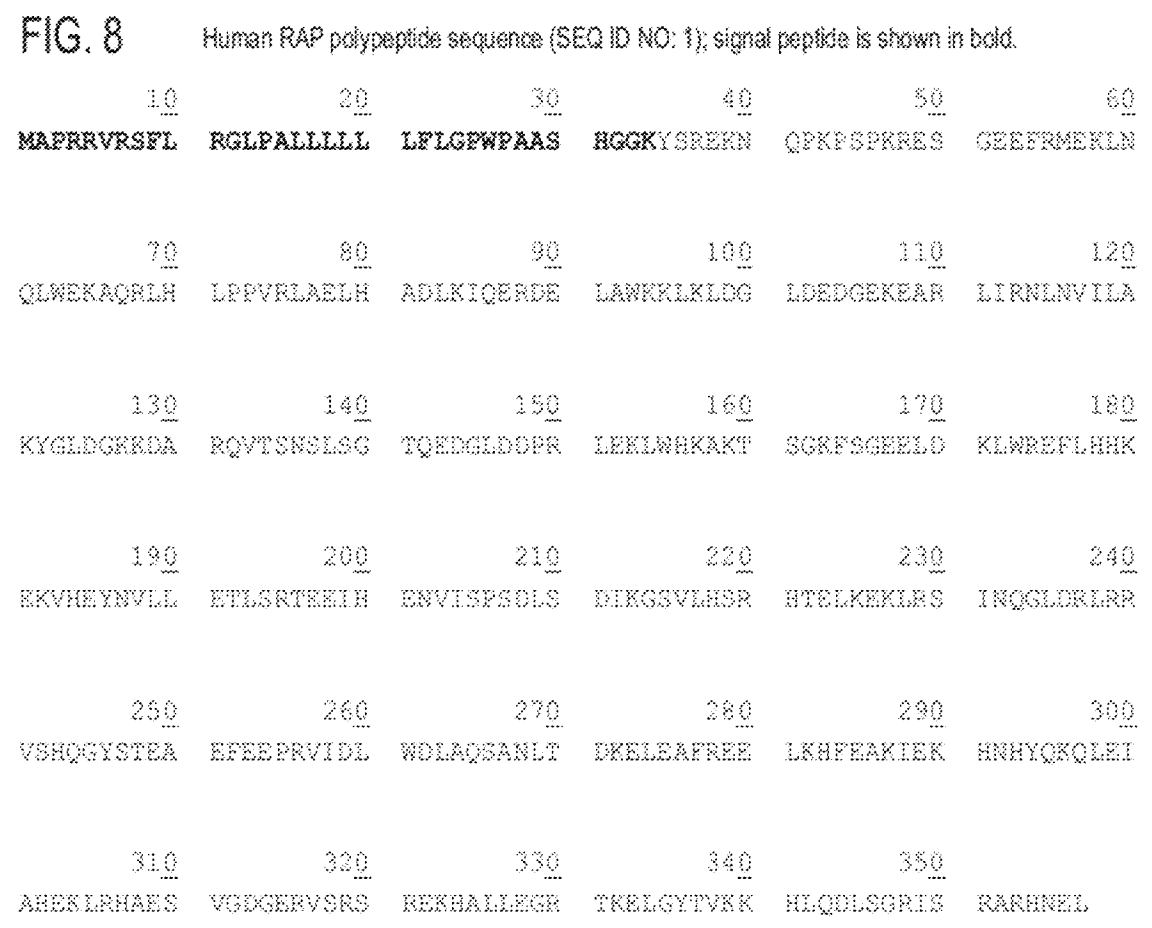

FIG. 8   Human RAP polypeptide sequence (SEQ ID NO: 1); signal peptide is shown in bold.

```
        10         20         30         40         50         60
MAPRRVRSFL RGLPALLLLL LFLGCWPAAS HGGKYSKRNN QPKPSPKRES GEEFRMEKLN
        70         80         90        100        110        120
QLWEKAQRLH LPPVRLAELH ADLKIQERDE LAWKKLKLDG LDEDGEKEAR LIRNLNVILA
       130        140        150        160        170        180
KYGLDGKKDA RQVTSNSLSG TQEDGLDDPR LEKLWHKAKT SGKFSGEELD KLWREFLHHK
       190        200        210        220        230        240
EKVHEYNVLL ETLSRTEEIH ENVISPSDLS DIKGSVLHSR HTELKEKLRS INQGLDRLRR
       250        260        270        280        290        300
VSHQGYSTEA EFEEPRVIDL WDLAQSANLT DKELEAFREE LKHFEAKIEK HNHYQKQLEI
       310        320        330        340        350
AHEKLRHAES VGDGERVSRS REKHALLEGR TKELGYTVKK HLQDLSGRIS RARHNEL
```

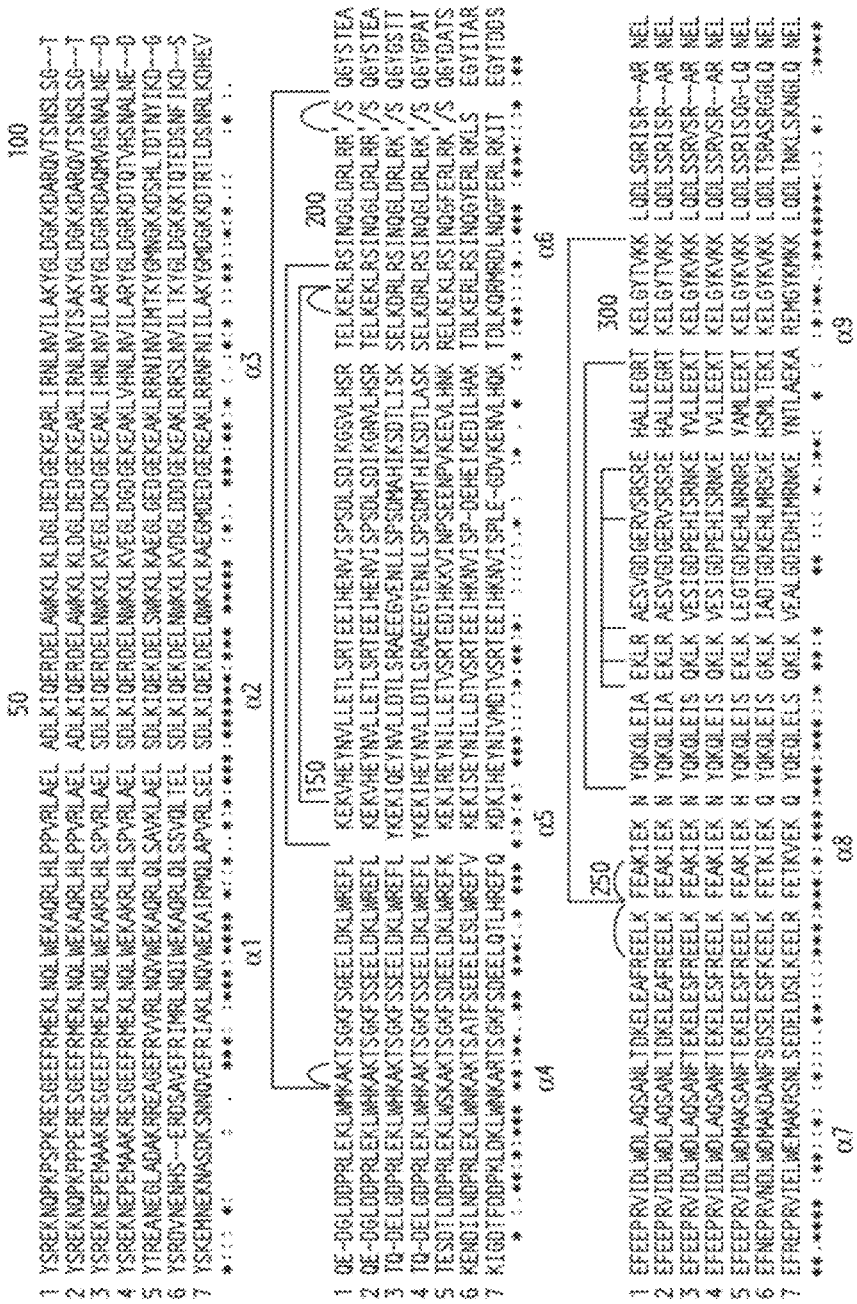
FIG. 9 Alignments of RAP polypeptide sequences from various species (provided by D. Strickland). SEQ ID NOs. 1-7

INHIBITION OF PRION PROPAGATION BY RECEPTOR ASSOCIATED PROTEIN (RAP), ITS DERIVATIVES, MIMETICS AND SYNTHETIC PEPTIDES

BACKGROUND

Prion diseases, otherwise known as Transmissible Spongiform Encephalopathies (TSEs), are a family of progressive neurodegenerative disorders that affect both humans and animals. They are distinguished by long incubation periods, characteristic spongiform changes associated with neuronal loss, and a failure to induce classic immune response. The causative agent of TSEs is believed to be a prion. A prion is a transmissible agent mostly consisting of a conformationally changed prion protein that is able to induce abnormal folding of normal cellular prion protein. Prion replication in the brain leads to brain damage and the characteristic signs and symptoms of the disease. Human prion diseases are rare, usually rapidly progressive and fatal; no preclinical diagnostic test or treatment is currently available.

The normal cellular prion protein is found in various organs and tissues throughout the body, including the brain, in healthy people and animals. However, prion protein found in the brains of disease-affected people or animals has a different "mis-folded" structure and is partially resistant to proteases. The normal cellular form of the prion protein is generally called $PrP^C$ (the "c" refers to "cellular"). The infectious form is variously called $PrP^{Sc}$ (the "Sc" is from "scrapie"); $PrP^{Sc, TSE, CJD, GSS, FFI, BSE, CWD, etc}$ (the Sc, TSE, CJD, GSS, FFI, and CWD refer to the abnormal protein of a TSE disease, and more specifically to scrapie, various forms of Creutzfeldt-Jakob disease, Gerstmann-Sträussler-Scheinker disease, fatal familial insomnia, bovine spongiform encephalopathy, chronic wasting disease, etc.); and more generally $PrP^d$ (the "d" refers to "disease-associated" prion protein).

Human $PrP^C$ is a 253-amino acid protein produced from a single-copy gene located on chromosome 20 (LIAO et al. "Human prion protein cDNA: molecular cloning, chromosomal mapping, and biological implications," Science, 1986, Vol. 233, pp. 364-367) which undergoes various posttranslational modifications that include formation of a disulphide bond (STAHL et al., "Prions and prion proteins," FASEB J., 1991, Vol. 5, pp. 2799-2807), glycosylation (RUDD et al., "Prion glycoprotein: structure, dynamics, and roles for the sugars," Biochemistry, 2001, Vol. 40, pp. 3759-66), removal of 22 amino acids from C-terminus and addition of glycophosphotidylinositol (GPI) moiety (STAHL et al., "; Cell, 1987, Vol. 51, pp. 229-40). The normal cellular protein is attached to the plasma membrane through a GPI anchor and has a predominantly alpha helical structure. The fully glycosylated protein has a molecular weight of 38 kDa, is monomeric in structure and sensitive to proteolysis (CAUGHEY et al., "Prions and their partners in crime," Nature, 2006, Vol. 443, pp. 803-10, Review). $PrP^C$ is known to interact with various proteins, including heat-shock proteins (EDENHOFER et al., "Prion protein PrPc interacts with molecular chaperones of the Hsp60 family," J Virol., 1996, Vol. 70, pp. 4724-8), a 37 kDa/67 kDa laminin receptor (RIEGER et al., "The human 37-kDa laminin receptor precursor interacts with the prion protein in eukaryotic cells," Nat Med., 1997, Vol. 3, pp. 1383-8; GAUCZYNSKI et al., "The 37-kDa/67-kDa laminin receptor acts as the cell-surface receptor for the cellular prion protein," EMBO J., 2001, Vol. 20, pp. 5863-75), stress-inducible protein-1 of 66 kDa predominantly present in cytoplasm (ZANATA et al., "Stress-inducible protein 1 is a cell surface ligand for cellular prion that triggers neuroprotection," EMBO J., 2002, Vol. 21, pp. 3307-16), plasminogen (ELLIS et al., "Plasminogen activation is stimulated by prion protein and regulated in a copper-dependent manner," Biochemistry, 2002, Vol. 41, pp. 6891-6; PRAUS et al., "Stimulation of plasminogen activation by recombinant cellular prion protein is conserved in the NH2-terminal fragment PrP23-110," Thromb Haemost., 2003, Vol. 89, pp. 812-9; KORNBLATT et al., "The fate of the prion protein in the prion/plasminogen complex," Biochem Biophys Res Commun., 2003, Vol. 305, pp. 518-22), a neuronal cell adhesion molecule (NCAM) (SANTUCCIONE et al., "Prion protein recruits its neuronal receptor NCAM to lipid rafts to activate p59fyn and to enhance neurite outgrowth," J Cell Biol., 2005, Vol. 169, pp. 341-54), heparan sulphate proteoglycans (HPSG) (HORONCHIK et al., "Heparan sulfate is a cellular receptor for purified infectious prions," J Biol Chem., 2005, Vol. 280, p. 17062, Epub., 2005 Jan. 24), the low-density lipoprotein receptor-related protein (LRP1) (TAYLOR et al., "Role of lipid rafts in the processing of the pathogenic prion and Alzheimer's amyloid-beta proteins," Semin Cell Dev Biol., 2007, Vol. 18, pp. 638-48, Epub., 2007 Jul. 24, Review; PARKYN et al., "LRP1 controls biosynthetic and endocytic trafficking of neuronal prion protein," J Cell Sci., 2008, Vol. 121(Pt 6), pp. 773-83, Epub., 2008 Feb. 19; Cervenakova et al., unpublished data, 2004), other LDL receptor superfamily members, megalin receptor and VLDLR (Cervenakova et al., unpublished data, 2004). It has been suggested that $PrP^C$ could function as a part of the LRP1 scavenger complex, because its N-terminal domain has multiple binding motifs (CAUGHEY et al., "Prions and transmissible spongiform encephalopathy (TSE) chemotherapeutics: A common mechanism for anti-TSE compounds?" Acc Chem Res., 2006, Vol. 39, pp. 646-53) and its hydrophobic sequence (amino acids 112-130) exposed to an aqueous environment could bind to denatured proteins as $PrP^C$ rapidly traffics across the neuronal surface. Recently, it has been shown that LRP1 binds to and is involved in both the biosynthetic and the endocytic trafficking of neuronal $PrP^C$ (PARKYN et al., "LRP1 controls biosynthetic and endocytic trafficking of neuronal prion protein," J Cell Sci., 2008, Vol. 121(Pt 6), pp. 773-83, Epub., 2008 Feb. 19). The function of the normal $PrP^C$ is not known, but there is evidence that it may function as a copper-dependent antioxidant, a signaling molecule, an anti- and pro-apoptotic molecule, as a protein supporting neuronal morphology and adhesion, and it may play a role in maintenance of long-term memory (ZOMOSA-SIGNORET et al., *Physiological role of the cellular prion protein*. Vet Res. 2008, Vol. 39:9. Epub., 2007 Nov. 27. Review). It has been recently proposed that $PrP^C$ is a marker of long-term bone marrow hematopoetic stem cells and supports their self-renewal (ZHANG et al., "Prion protein is expressed on long-term repopulating hematopoietic stem cells and is important for their self-renewal," Proc Natl Acad Sci, USA, 2006, Vol. 103, pp. 2184-9, Epub., 2006 Feb. 7).

No differences in the primary structure (i.e. amino acid sequence) of $PrP^C$ and $PrP^d$ have been detected, nor have any differences been found between PrP genes or mRNAs from normal and infected brains with respect to structure or copy number. The physical differences (such as three-dimensional configuration) between the two proteins are therefore attributed to post-translational chemical modification. However, familial prion disease can occur in families with a mutation in the PrP gene, and mice with PrP mutations develop prion disease despite controlled conditions where transmission is prevented (HSIAO et al., "Spontaneous neurodegeneration in transgenic mice with prion protein codon 101 proline—leucine substitution," Ann N Y Acad Sci., 1991, Vol. 640, pp.

166-70). Many different mutations have been identified and it is hypothesized that the mutations somehow make PrP$^C$ more likely to change spontaneously into the abnormal PrP$^d$ form.

PrP$^d$ is able to convert normal PrP$^C$ proteins into the infectious isoform by changing their conformation, or shape; this, in turn, alters the way the proteins interconnect. Data from animal transmission studies has pointed to the existence of an unidentified factor, termed "protein X," which may control the conversion process (TELLING et al., "Prion propagation in mice expressing human and chimeric PrP transgenes implicates the interaction of cellular PrP with another protein," Cell, 1995, Vol. 83, pp. 79-90). Although the exact 3D structure of PrP$^d$ is not known, during the refolding of PrP$^C$ into PrP$^d$, some of the normal α-helical protein structure is partially converted into β-sheet. Aggregations of these abnormal isoforms form highly structured amyloid fibers, which accumulate to form plaques consisting of tightly packed β-sheets. Unlike PrP$^C$, this altered structure is extremely stable and accumulates in infected tissue. This stability means that prions are largely resistant to denaturation by chemical and physical agents, making disposal and containment of the particles difficult. The term "PrP$^{res}$" (the "res" is from "resistant") is generally used to refer to the resistant proteolytic cleavage product of PrP$^d$ after treatment with Proteinase K.

Prions cause neurodegenerative disease by damaging neurons within the central nervous system and disrupting the normal tissue structure. While the incubation period for prion diseases is generally quite long, once symptoms appear the disease progresses rapidly, leading to brain damage and death. All known prion diseases are currently untreatable and fatal. Many different mammalian species can be affected by prion diseases. Due to the minor differences in PrP between different species, it is not unusual for a prion disease to be transmitted from one species to another. However, species to species transmission can only occur under certain conditions, and mechanisms of the transmission are not fully understood. The most recent example of such transmission is variant Creutzfeldt-Jakob disease (vCJD) affecting humans, which is believed to be caused by a prion which typically infects cattle, causing bovine spongiform encephalopathy (BSE), that was transmitted through contaminated bovine-derived food products (WILL et al., "A new variant of Creutzfeldt-Jakob disease in the UK," Lancet, 1996, Vol. 347, pp. 921-5).

The primary route of natural TSE infection, for example scrapie in sheep and goats, BSE in cattle and sheep, CWD in deer and elk, and vCJD in humans, is thought to be through ingestion of contaminated sources. Prions may be deposited in the environment through the remains of dead animals and via urine, saliva, and other body fluids (e.g. in the case of CWD) (HALEY et al., "Detection of CWD prions in urine and saliva of deer by transgenic mouse bioassay," PLoS ONE, 2009, Vol. 4, p. 4848, Epub., 2009 Mar. 18). They may then linger in the soil by binding to clay and other minerals (SAUNDERS et al., *Prions in the environment: occurrence, fate and mitigation*. Prion. 2008 Vol. 2:162-9. Epub 2008 Oct. 26. Review.). Other methods of infection are also known.

Low density lipoprotein receptor-related protein associated protein 1, also known as LRPAP1 or Receptor-Associated Protein (RAP), is encoded in humans by the LRPAP1 gene (STRICKLAND et al., "*Primary structure of alpha 2-macroglobulin receptor-associated protein. Human homologue of a Heymann nephritis antigen*". J. Biol. Chem., 1991 Vol. 266, pp. 13364-9. KORENBERG et al., "Chromosomal localization of human genes for the LDL receptor family member glycoprotein 330 (LRP2) and its associated protein RAP (LRPAP1)". *Genomics* 1994, Vol. 22, pp. 88-93. The protein was first isolated from mice as a 44-kD heparin-binding protein and was initially termed HBP-44 (FURUKAWA et al., "A heparin binding protein whose expression increases during differentiation of embryonal carcinoma cells to parietal endoderm cells: cDNA cloning and sequence analysis," J. Biochem., 1990, Vol. 108, No. 2, pp. 297-302). In humans a 39-kD associated protein was purified as a part of the alpha-2-macroglobulin receptor complex (ASHCOM et al., "The human alpha 2-macroglobulin receptor: identification of a 420-kD cell surface glycoprotein specific for the activated conformation of alpha 2-macroglobulin," J. Cell. Biol., 1990, Vol. 110, pp. 1041-8; STRICKLAND et al., "Primary structure of alpha 2-macroglobulin receptor-associated protein. Human homologue of a Heymann nephritis antigen," J Biol Chem., 1991, Vol. 266, pp. 13364-9. The primary structure of the 39-kD polypeptide, termed alpha-2-macroglobulin receptor-associated protein ($α_2$MRAP), was determined by cDNA cloning (STRICKLAND et al., "Primary structure of alpha 2-macroglobulin receptor-associated protein. Human homologue of a Heymann nephritis antigen," J Biol Chem., 1991, Vol. 266, pp. 13364-9). Functional studies revealed that RAP blocked ligand binding by LRP1 (HERZ et al., "39-kDa protein modulates binding of ligands to low density lipoprotein receptor-related protein/alpha 2-macroglobulin receptor," J. Biol. Chem., 1991, Vol. 266, pp. 21232-8; WILLIAMS et al., "A novel mechanism for controlling the activity of alpha 2-macroglobulin receptor/low density lipoprotein receptor-related protein. Multiple regulatory sites for 39-kDa receptor-associated protein," Biol Chem., 1992, Vol. 267, pp. 9035-40). The deduced amino acid sequence of human RAP contains a putative signal sequence that precedes the 323-residue mature protein. The sequence showed 73% identity with a rat protein and 77% identity to a 44-kD mouse HBP-44. There are also similarities between RAP and apolipoprotein E. RAP is localized in the rough endoplasmic reticulum where it binds to LDL-receptor related proteins functioning as a specialized chaperone assisting in the folding and intracellular transport of members of the LDL receptor family. RAP is expressed in various organs and tissues throughout the body, including the brain. Experimental evidence suggests that RAP acts as a receptor antagonist and prevents association of newly synthesized LDL-receptor related proteins with their ligands during transport to the cell surface (WILLNOW, "Receptor-associated protein (RAP): a specialized chaperone for endocytic receptors," Biol Chem., 1998, Vol. 379, pp. 1025-31). RAP is efficiently transferred across the blood-brain barrier and may provide a means of protein-based drug delivery to the brain (PAN et al., "Efficient transfer of receptor-associated protein (RAP) across the blood-brain barrier," J Cell Sci., 2004, Vol. 117(Pt 21), pp. 5071-8, Epub., 2004 Sep. 21). Recently, the importance of RAP has been shown in amyloid depositions in a mouse model of Alzheimer's disease (XU et al. "Receptor-associated protein (RAP) plays a central role in modulating Abeta deposition in APP/PS 1 transgenic mice," PLoS ONE, 2008, Vol. 3, p. 3159). RAP also inhibited beta-amyloid protein (Abeta)oligomerization, neurotoxic effects of Abeta in cell cultures and blocked an Abeta-induced inhibition of long-term memory consolidation in 1-day-old chicks (KERR et al., "*Inhibition of Abeta aggregation and neurotoxicity by the 39-kDa receptor-associated protein*", J Neurochem. 2010 Vol. 112:1199-209. Epub 2009 Dec. 10).

SUMMARY

A method for prophylaxis or treatment of a prion disease in a subject comprises administering to the subject a therapeutically effective amount of an agent selected from the group consisting of an RAP polypeptide and a derivative, variant, fragment, and mimetic thereof. The subject may be one who is at risk of developing, or is infected with, or is otherwise suffering from a prion disease.

In an exemplary embodiment, the prion disease is selected from the group consisting of various forms of Creutzfeldt-Jakob disease (CJD) such as iatrogenic Creutzfeldt-Jakob disease (iCJD), variant Creutzfeldt-Jakob disease (vCJD), familial Creutzfeldt-Jakob disease (fCJD), sporadic Creutzfeldt-Jakob disease (sCJD)); Gerstmann-Sträussler-Scheinker syndrome (GSS); Fatal insomnia familial (FFI) and sporadic; Kuru, Scrapie, Bovine spongiform encephalopathy (BSE); Transmissible mink encephalopathy (TME); Chronic wasting disease (CWD); Feline spongiform encephalopathy; and Exotic ungulate encephalopathy (EUE).

The subject can be a mammal, and the mammal can be selected from the group consisting of humans, sheep, goats, cows, mink, white-tailed deer, elk, mule deer, moose, cats, nyala, gemsbok, oryx, eland, kudu, ankole, and bison. In an exemplary embodiment, the mammal is a human.

Examples of suitable agents include polypeptide sequences comprising the following RAP sequences: amino acids 35-357 of SEQ ID NO: 1, amino acid sequences having at least 70% to 100% sequence identity to amino acids 35-357 of SEQ ID NO: 1, and any one of SEQ ID NOS: 1-7. In an exemplary embodiment, the agent comprises amino acids 35-357 of SEQ ID NO: 1.

BRIEF DESCRIPTION OF THE DRAWINGS

FIG. 1 shows the effect of RAP on $PrP^{res}$ formation in spleen-derived mo-vCJD-SP/63 and control SP/76 cell lines 24 hours after treatment.

FIG. 2 shows the effect of 1 μM RAP on $PrP^{res}$ formation in spleen-derived mo-vCJD-SP/63 cell line (time-course).

FIG. 3 shows the effect of RAP on $PrP^{res}$ formation in spleen-derived mo-vCJD-SP/63 cell line (dose-dependent inhibition).

FIG. 4 shows the effect of 500 nM RAP on $PrP^{res}$ formation in spleen-derived mo-vCJD-SP/63 and Fu-SP/58 cell lines persistently infected with either mo-vCJD or Fukuoka.

FIG. 5 shows the effect of 500 nM RAP on $PrP^{res}$ formation in spleen-derived mo-vCJD-SP/63 cell line (time-course).

FIG. 6 shows the inhibitory effect of 500 nM RAP on $PrP^{res}$ formation in bone-marrow-derived cell line 336-2BMS-Fu2 persistently infected with Fukuoka.

FIG. 7 shows the inhibitory effect of multiple treatments with 250 nM RAP on $PrP^{res}$ formation in bone marrow-derived 336-2-BM-Fu2 cell line persistently infected with Fukuoka.

FIG. 8 shows the human RAP polypeptide sequence, including the signal peptide (SEQ ID NO: 1).

FIG. 9 shows sequence alignments for RAP polypeptides from various species. In the figure, the sequences identified as 1-7 are from human (amino acids 35-357 of SEQ ID NO: 1), African clawed frog (SEQ ID NO: 2), zebrafish (SEQ ID NO: 3), orangutan (SEQ ID NO: 4), mouse (SEQ ID NO: 5), rat (SEQ ID NO: 6), and chicken (SEQ ID NO: 7), respectively.

DETAILED DESCRIPTION

We have discovered that Receptor-Associated Protein (RAP), also known as low density lipoprotein receptor-related protein associated protein 1 or LRPAP1 is a potent inhibitor of replication of various TSE agents, and particularly replication of mis-folded prion protein or $PrP^d$.

The phenomenon of mis-folded prion proteins is associated with a wide variety of prion diseases, including, but not limited to, those generally referred to as TSEs.

RAP and its variants, derivatives, fragments, and/or mimetics (also referred to herein as "RAP agents") are useful in the prophylaxis and/or treatment of prion diseases in various organisms, particularly mammals. Notably, RAP agents can be used to prevent, treat, or delay the onset or progression of prion disease, and can do so regardless whether the prion disease is caused by infection from another organism or by genetic mutation.

According to various embodiments, RAP and its variants, derivatives, fragments, and/or mimetics may be administered to a diseased or at risk animal by varied means and in various forms. In one embodiment, a RAP agent is administered via intranasal delivery or parenterally. The RAP agent may be compounded as a pharmaceutical formulation in aqueous media.

In one embodiment, the RAP agent is formulated for injection as an aqueous mixture that is about 2 μM RAP. Such formulations can be administered to the subject in volumes of about 30 ml to about 3 μl. In another embodiment, the formulation is administered to the subject at about 3 ml to about 3 μl of a 2 μM RAP solution, or an equivalent dose. As discussed elsewhere, the administration of such doses can be made intranasally or by parenteral injection.

As used herein, the terms "cellular prion protein," "normal prion protein" or "$PrP^C$" mean prion proteins in their normal (or wild-type) state and include the naturally occurring prion protein and its variants.

The terms "disease-associated prion protein," "mis-folded prion protein," and "$PrP^d$" mean the infectious isoform, and refer to a prion protein which has undergone a three-dimensional structural change resulting in increased β-sheet structure, decreased solubility, and/or increased proteolytic resistance when compared with its normal state (i.e., that not associated with disease). The term "$PrP^{res}$" indicates the proteolytic cleavage product or digestion product of $PrP^d$.

By "prion diseases" or "prion disorders" is meant those disorders associated with or caused by the conversion of $PrP^C$ into $PrP^d$ and/or the consequent aggregation of prion proteins. The term "prion diseases" is used herein interchangeably with "TSE" (transmissible spongiform encephalopathies) or spongiform encephalopathies. Prion diseases affect humans and other mammals, including livestock.

In humans, prion diseases include Creutzfeldt-Jakob disease (CJD) and its varieties (e.g. iatrogenic Creutzfeldt-Jakob disease (iCJD), variant Creutzfeldt-Jakob disease (vCJD), familial Creutzfeldt-Jakob disease (fCJD), and sporadic Creutzfeldt-Jakob disease (sCJD)); Gerstmann-Sträussler-Scheinker syndrome (GSS); Fatal familial insomnia (FFI); sporadic fatal insomnia; and Kuru.

In animals, the diseases include Scrapie (sheep and goats), Bovine spongiform encephalopathy (BSE, known as "mad cow disease") (cattle); Transmissible mink encephalopathy (TME) (mink); Chronic wasting disease (CWD) (white-tailed deer, elk, mule deer and moose); *Feline* spongiform encephalopathy (cats, e.g. domestic cat, puma, cheetah, ocelot, tiger); Exotic ungulate encephalopathy (EUE) or spongiform encephalopathy of exotic ruminants (nyala, gemsbok, oryx (e.g. Arabian oryx and scimitar-horned oryx), eland, kudu (e.g. greater kudu), ankole, and bison); and (possibly) Spongiform encephalopathy of the ostrich (ostrich).

RAP refers to Receptor-Associated Protein, also known as low density lipoprotein receptor-related protein associated protein 1 or LRPAP1, regardless of the species of origin. In an exemplary embodiment, RAP is the full-length human RAP polypeptide sequence, minus the signal sequence (amino acids 35-357 of SEQ ID NO: 1; see FIG. 8 and STRICKLAND et al., "Primary structure of alpha 2-macroglobulin receptor-associated protein. Human homologue of a Heymann nephritis antigen," J Biol Chem., 1991, Vol. 266, pp. 13364-9), as used in the present examples.

As used herein, the term "RAP" includes any naturally-occurring RAP polypeptide sequence, such as a mammalian or a non-mammalian RAP polypeptide sequence. The term "RAP polypeptide" as used herein refers to full-length RAP sequences of natural origin as well as truncated forms, e.g., amino acids 35-357 of SEQ ID NO: 1, and those having at least 90% homology to a RAP sequence of natural origin.

Amino acid sequences of RAP from various mammalian and non-mammalian species have been identified (see, e.g., the sequences for human (amino acids 35-357 of SEQ ID NO: 1); African clawed frog (SEQ ID NO: 2); zebrafish (SEQ ID NO: 3); orangutan (SEQ ID NO: 4); mouse (SEQ ID NO: 5); rat (SEQ ID NO: 6); and chicken (SEQ ID NO: 7); identified as sequences 1-7, respectively, in FIG. 9); as well as Common Chimpanzee, *Macaca mulatta*—Rhesus macaque, *Bos Taurus*—Cow, *Capra hircus*—Goat, *Ovis aries*—Sheep, *Sus scrofa*—Pig, *Canis lupus familiaris*-Dog. RAP sequences can also be found in the literature, e.g., GenBank, according to the following accession numbers: Human [GenBank Acc: NM_002337]; *Pan troglodytis*—Common Chimpanzee [GenBank Acc: XM_517082]; Pongo abeli-Sumatran Orangutan [GenBank Acc: NM_001131664.1]; *Macaca mulatta*—Rhesus macaque [GenBank Acc: XM_001085674]; *Bos Taurus*—Cow [GenBank Acc: NM_001080225]; *Capra hircus*—Goat [GenBank Acc: EV438413]; *Ovis aries*—Sheep [Assembled from the 4 EST clones, GenBank Acc. numbers: GO756662.1; GO772827.1; 114717509; 88624253]; *Sus scrofa*—Pig [GenBank Acc: NM_001113436]; *Canis lupus familiaris*-Dog [GenBank Acc: XM_536218]; *Mus musculus*—Mouse [GenBank Acc: NM_013587]; *Rattus norvegicus*—Rat [GenBank Acc: NM_001169113]; *Gallus gallus*—Chicken [GenBank Acc: NM_205062]; *Danio rerio*—Zebrafish [GenBank Acc: NM_201306]; *Xenopus laevis*—African clawed frog [GenBank Acc: BC054293]. The following also demonstrate homology to the foregoing RAP sequences: *Drosophila melanogaster*-Fruit fly; Gene symbol: CG8507; GenBank Acc: NP_649950.1; *Anopheles gambiae*—Mosquito; Gene symbol: AgaP_AGAP003521; GenBank Acc: XP_313261.4; *Caenorhabditis elegans*—Worm; hypothetical protein with gene symbol C15C8.4, GenBank Acc: NP_506187.2.

The term "RAP agents" includes RAP as well as derivatives, variants, fragments, or mimetics of RAP that inhibit $PrP^d$ formation and/or promote the transformation of $PrP^d$ to non-infectious form(s).

RAP agents include polypeptides with significant sequence homology to amino acids 35-357 of SEQ ID NO: 1, such as from about 70% to about 100% sequence identity to amino acids 35-357 of SEQ ID NO: 1 (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with amino acids 35-357 of SEQ ID NO: 1).

In one embodiment, there is a method for prophylaxis and/or treatment of a mammal at risk of or suffering from a prion disease, comprising administering to the mammal a therapeutically effective amount of an agent selected from the group consisting of: mammalian RAP polypeptide; and a derivative, variant, fragment, and mimetic thereof; and combinations thereof. The prion disease may be selected from the group of various forms of Creutzfeldt-Jakob disease (CJD), iatrogenic Creutzfeldt-Jakob disease (iCJD), variant Creutzfeldt-Jakob disease (vCJD), familial Creutzfeldt-Jakob disease (fCJD), sporadic Creutzfeldt-Jakob disease (sCJD)); Gerstmann-Sträussler-Scheinker syndrome (GSS); Fatal insomnia, familia (FFI) or sporadic; Kuru, Scrapie, Bovine spongiform encephalopathy (BSE); Transmissible mink encephalopathy (TME); Chronic wasting disease (CWD); *Feline* spongiform encephalopathy; and Exotic ungulate encephalopathy (EUE). The mammal may be selected from the group of human, sheep, goat, cow, mink, white-tailed deer, elk, mule deer, moose, cat, nyala, gemsbok, oryx, eland, kudu, ankole, and bison.

The therapeutically effective agent may be selected from the group of: a) a polypeptide comprising amino acids 35-357 of SEQ ID NO: 1; b) a polypeptide comprising an amino acid sequence having 70% to 100% sequence identity to amino acids 35-357 of SEQ ID NO: 1; and c) a polypeptide comprising an amino acid sequence of SEQ ID NO: 2, SEQ ID NO: 3, SEQ ID NO: 4, SEQ ID NO: 5, SEQ ID NO: 6, or SEQ ID NO: 7; as well as the RAP sequences (also disclosed herein) of: Common Chimpanzee, *Macaca mulatta*—Rhesus macaque, *Bos Taurus*—Cow, *Capra hircus*—Goat, *Ovis aries*—Sheep, *Sus scrofa*—Pig, *Canis lupus familiaris*-Dog.

In another embodiment, the method of prophylaxis and/or treatment further includes intranasal administration of a therapeutically effective amount of a RAP agent in an aqueous vehicle. In one embodiment, the RAP agent is a polypeptide comprising amino acids 35-357 of SEQ ID NO: 1. The administration of the RAP agent can be repeated until a diminution or eradication of symptoms is achieved, or until the subject is no longer exposed or at risk of contracting a prion disease.

The terms "treatment" or "treating" and the like are used herein to generally mean obtaining a desired pharmacological and/or physiological effect, and refer to complete elimination as well as to any clinically or quantitatively measurable reduction in the symptoms of the prion disease for which the subject is being treated. The effect may be prophylactic in terms of completely or partially preventing a disease or symptom thereof, and/or may be therapeutic in terms of a partial or complete cure for a disease and/or adverse effects attributable to the disease. The effect may also relate to reversing or delaying progression of a prion disease or symptom thereof. Thus, for example, treatment may indicate that any symptoms of a prion disease are reduced or alleviated; the conversion of $PrP^C$ into $PrP^d$ is inhibited; and/or the processing of $PrP^d$ into non-infectious fragments is promoted by administration of the agent (i.e. RAP and derivatives, variants, fragments, and mimetics thereof) described herein.

A "therapeutically effective amount" or "pharmaceutically effective amount" means the amount of an agent that, when administered to a subject in need thereof, is sufficient to effect such treatment. Thus a "therapeutically effective amount" is an amount indicated for treatment while not exceeding an amount which may cause significant adverse effects (commensurate with a reasonable risk/benefit ratio). The "therapeutically effective amount" will vary depending on the agent, and will also be determined by physical and physiological factors such as the age, body weight, and/or clinical history of the subject to be treated. Methods for evaluating the effectiveness of therapeutic treatments are known to those of skill in the art.

A "subject in need thereof" refers to any subject or individual who could benefit from the method of treatment described herein, and includes those that are infected, suffering from, or at risk of developing a prion disease. In some embodiments, a subject in need thereof is a subject predisposed for the development of a prion disease; a subject exposed to infection with a prion disease; a subject having one or more prion diseases but not exhibiting any clinical symptoms; and/or a subject exhibiting one or more symptoms of one or more prion diseases.

The "subject in need thereof" is generally a vertebrate, such as a mammal. Mammals include, but are not limited to, humans, other primates, farm animals, exotic animals, sport animals and pets. Examples include sheep, goats, cows, mink, white-tailed deer, elk, mule deer, moose, cats (e.g. domestic cat, puma, cheetah, ocelot, tiger), nyala, gemsbok, oryx (e.g. Arabian oryx and scimitar-horned oryx), eland, kudu (e.g. greater kudu), ankole, and bison. In an exemplary embodiment, the subject is a human. In other embodiments, the methods find use in experimental animals, in veterinary application, and/or in the development of animal models for disease.

As used herein, the term "administering" or "introducing" an agent to a subject means providing the agent to a subject in a therapeutically effective manner. Methods of administering RAP agents to a subject includes a number of known means including, but not limited to, systemic administration (e.g. parenteral administration (intravenous, subcutaneous, or intramuscular), intraperitoneal administration, inhalation, transdermal delivery, oral delivery, nasal delivery, rectal delivery, etc.) and/or local administration (e.g. direct injection into a target tissue, delivery into a tissue via cannula, delivery into a target tissue by implantation of a time-release material, or delivery through the skin via a topical composition such as a cream, lotion, or the like), delivery into a tissue by a pump, etc., intraosseously, in the cerebrospinal fluid, or the like. The terms "orally" and "oral delivery" refer to administration by mouth and include ingestion of the formulation as well as oral gavage. Additional modes of administration include ocular (e.g. via eye drops), buccal, sublingual, vaginal, subcutaneous, or intradermal administration. In an exemplary embodiment, the target tissue is the brain.

Modes of administration include delivery via a sustained release and/or controlled release drug delivery formulation and/or device. "Sustained release" refers to release of a drug or an active metabolite thereof into the systemic circulation over a prolonged period of time relative to that achieved by oral administration of a conventional formulation of the drug. "Controlled release" is a zero order release; that is, the drug releases over time irrespective of concentration. Single, multiple, continuous or intermittent administration can be effected.

One skilled in the art will appreciate that the RAP agent can be formulated in a variety of styles, and using a wide variety of carriers, solvents, diluents, and other excipients. For example, the RAP agent can be formulated in an aqueous mixture or solution. The mixture may further include excipients such as buffers, preservatives, antioxidants, and the like all in accordance with commonly accepted principles of pharmaceutical formulation. Additionally, the RAP agent can be formulated as a cream, an oil, a solid release form, or in a patch, e.g., for transdermal delivery.

Doses to be administered are variable according to the treatment period, frequency of administration, the host, and the nature and severity of the disorder. The dose can be determined by one of skill in the art without an undue amount of experimentation. The agents are administered in dosage concentrations sufficient to ensure the release of a sufficient dosage unit into the patient to provide the desired treatment of the prion disease. The active ingredients may be administered to achieve therapeutic or prophylactic blood concentrations, such as in vivo plasma concentrations of the agents of from about 0.01 to about 10,000 ng/cc, such as from about 0.01 to about 1,000 ng/cc. "Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

For example, the methods described herein may use compositions to provide from about 0.01 to about 100 mg/kg body weight/day of the agents, from about 0.01 to about 10 mg/kg body weight/day of the agents, or about 30 mg/kg body weight/day of the agents. It will be understood, however, that dosage levels that deviate from the ranges provided may also be suitable in the treatment of a given disorder.

The agents may be in any form suitable for administration. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained- and/or controlled release forms thereof. The desired dose may be provided in several increments at regular intervals throughout the day, by continuous infusion, or by sustained and/or controlled release formulations, or may be presented as a bolus, electuary or paste.

"Practical dosage regimen" refers to a schedule of drug administration that is practical for a patient to comply with. For human patients, a practical dosage regimen for an orally administered drug is likely to be an aggregate dose of less than 10 g/day.

In one embodiment, a pharmaceutical composition or formulation comprising the agents is prepared by admixture with one or more pharmaceutically acceptable carriers. Other products may be added, if desired, to maximize agent preservation, or to optimize a particular method of delivery. In addition, the present methods include use of combination compositions comprising the agents as described herein in combination with other agents suitable for the treatment of prion diseases.

"Pharmaceutically acceptable carrier" or "diluent" means a carrier that is useful in preparing a pharmaceutical composition that is generally safe, neither biologically nor otherwise undesirable, not toxic or otherwise unacceptable commensurate with a reasonable risk/benefit ratio, compatible with other ingredients of the formulation, and includes a carrier that is acceptable for veterinary use as well as human pharmaceutical use. "A pharmaceutically acceptable carrier" as used in the specification and claims includes both one and more than one such carrier.

A "pharmaceutically acceptable carrier" includes any and all solvents, dispersion media, coatings, antibacterial and anti-fungal agents, isotonic and absorption delaying agents, and the like, compatible with pharmaceutical administration of a composition comprising agents. Examples of such carriers or diluents include, but are not limited to, water, saline, Ringer's solutions and dextrose solution. The volume of the pharmaceutical composition is based on the intended mode of administration and the safe volume for the individual patient, as determined by a medical professional.

The present disclosure relates to use of any one or more of the agents described herein for the treatment of a prion disease. The present disclosure also relates to the use of any one or more of the agents described herein for manufacture of a medicament, particularly the manufacture of a medicament for treating a prion disease.

RAP agents, including RAP and its various mimetics, can also be used as a surface active agent for TSE disinfection. RAP inhibits or prevents or destroys $PrP^d$ replication by acting, at least in part, at the cell surface. By placing a RAP agent in contact with any of the various forms of $PrP^d$ (or TSE, e.g., BSE, CWD, CJD, scrapie, etc.), the RAP agent inhibits or destroys replication, and thus significantly reduces or eliminates or prevents $PrP^d$ infection. The RAP agent can be used as a TSE disinfectant on a host of surfaces including man-made surfaces as are found in a hospital or dwelling (e.g., metal or plastic devices, ceramics), those used in association with livestock including barns or rendering plants, as well as on natural surfaces such as grass, soil, etc.

The surface active agent can be applied as a surface coating, or it can be embedded in the surface material to be treated. For example, the RAP agent can be embedded in a polymer, ceramic, or composite material forming the structural elements of the surface to be disinfected; or it can be applied to a surface in a matrix as in a paint, varnish, polymer, gel, paste, oil, ointment, or other coating. The RAP agent disinfectant can also be formulated in a variety of embodiments, including a solution for liquid, aerosol, or spray administration, or as a slurry, powder, or paste.

The various matrixes or vehicles in which the RAP agent is compounded may be further formulated to include agents such as buffers, preservatives, excipients, or other known agents useful for protection of e.g., polypeptides, from light, heat, oxidation, free-radicals, and the like. The manner of formulation, the vehicle, and the ultimate disposition or means of application is not thought to be particularly significant, and are subject to development and manipulation according to known principles and methods.

RAP agents can be used in a method of TSE disinfection by administering a RAP agent to a material or surface likely to be contaminated with or exposed to a TSE. The RAP agent disinfectant can be used to treat areas in and around those used to house animals. The material or surface to be disinfected can be those likely to contact or harbor TSEs, and particularly those associated with, or exposed to food, including livestock feed, and may include the food itself, as well as materials used to store, transport, or process the food. In this manner, the methods include both a prophylactic effect, and therapeutic effect as the treatment of food can be used to disinfect the food, and can be a means of administration to the animal ingesting the food. As used herein, the term "animal" includes human.

Additionally, the TSE disinfectant described herein can be readily and inexpensively compounded for wide scale administration to animals in the wild, and so can be used to fight the spread of CWD. In such an embodiment, the RAP agent can be compounded, e.g., as an aqueous mixture, alone or with other excipients and/or additives, and sprayed over areas where TSE-infected animals, or animals at risk of TSE infection, are living and/or feeding.

As used herein, the singular forms "a", "an", and "the" include plural referents unless the context clearly dictates otherwise. Thus, for example, reference to "an RAP" includes a plurality of RAP molecules and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference.

While the disclosure has been described in detail with reference to certain embodiments thereof, it will be apparent to one skilled in the art that various changes can be made, and equivalents employed, without departing from the scope of the disclosure. In addition, the following examples are illustrative of the methods described herein and should not be considered as limiting the foregoing disclosure in any way.

EXAMPLES

The experiments set forth herein demonstrate that RAP inhibits $PrP^d$ formation in prion infected murine cell cultures of bone marrow and spleen origin. The inhibition of $PrP^d$ formation was observed over a time course of exposure to various concentrations of RAP. $PrP^d$, unlike $PrP^C$, is partially resistant to proteolysis by proteinase K. Thus, the formation of $PrP^d$ was determined by testing for the presence of $PrP^{res}$, the digestion product of $PrP^d$. $PrP^{res}$ is a recognized marker of prion infection.

The results show that a suitable treatment time for the cell cultures is between 12 and 24 hours, with an inhibitory concentration of between 50 and 250 nM. Multiple treatments inhibited $PrP^d$ formation at least through 20 passages (~70 days after the treatment was stopped). A similar approach has been used to treat other TSE infected cells with various substances including monoclonal anti-PrP-specific antibodies, and in in vivo experiments showing the delay in development of the disease in mice treated with such substances (CAUGHEY et al., "Prions and transmissible spongiform encephalopathy (TSE) chemotherapeutics: A common mechanism for anti-TSE compounds?" Acc Chem Res., 2006, Vol. 39, pp. 646-53; PANKIEWICZ et al., "Clearance and prevention of prion infection in cell culture by anti-PrP antibodies," Eur J Neurosci., 2006, Vol. 23, pp. 2635-47; and TELLING et al., "Prion propagation in mice expressing human and chimeric PrP transgenes implicates the interaction of cellular PrP with another protein," Cell, 1995, Vol. 83, pp. 79-90).

The murine spleen-derived stromal cell (SP) lines (Holland Laboratory) used in the experiments were developed to persistently propagate mouse-adapted human prion agents, Fukuoka-1 (Fu) (cell line Fu-SP/58) and mouse-adapted variant Creutzfeldt-Jakob disease (cell line mo-vCJD-SP/63) (AKIMOV et al., "Persistent propagation of variant Creutzfeldt-Jakob disease agent in murine spleen stromal cell culture with features of mesenchymal stein cells," J Virol., 2008, Vol. 82, pp. 10959-62, Epub., 2008 Aug. 20). The murine bone marrow (BM) stromal cell line (Holland Laboratory) also used in experiments was developed to persistently propagate Fu (cell line 336-2BMSFu2) (AKIMOV et al., "Murine bone marrow stromal cell culture with features of mesenchymal stem cells susceptible to mouse-adapted human TSE agent, Fukuoka-1," Folia Neuropathol. 2009, Vol. 47, pp. 205-14).

Experiment 1

The initial experiment was performed to determine if treatment of mo-vCJD-SP/63 cell cultures with low density lipoprotein receptor-related protein (LRP) specific polyclonal antibodies 2629, PrP specific monoclonal antibodies 6D11, or RAP have any effect on levels of total PrP and $PrP^{res}$.

Cell line mo-vCJD-SP/63 propagating PrP$^{res}$ through multiple passages, and control uninfected cell line SP/76, expressing normal $PrP^{C}$, were plated at a density of 1:3 of confluent monolayer. On the next day the growth medium was exchanged for fresh medium containing either 1 μM RAP (gift of Dr. Strickland), or 10 μg/ml 6D11 monoclonal antibody (Signet) or 50 μg/ml 2629 rabbit polyclonal antibody (gift of Dr. Strickland) or 3 μl control anti-alpha-tubulin rabbit polyclonal antibodies (Cell Signaling Tech). After 8 hours of incubation, an additional 0.5 μM RAP was added only to the cells which were already exposed to RAP. During each experiment, cell cultures were maintained at 37° C. in the presence of 5% $CO_2$. Cells were harvested using lysis buffer after 24 hours following initial treatment. A portion of the sample was treated with proteinase K (10 μg/ml) for digestion of normal PK-sensitive $PrP^{C}$ and another portion was left untreated. The proteins in PK-treated and untreated samples were precipitated by methanol at −80° C. After centrifugation the pellets were solubilized in a denaturing buffer containing 2% SDS, 62.5 mM Tris-HCl, 25% glycerol and 0.1% bromophenol blue, resolved on NuPAGE, 4-12% Bis-Tris gradient gel, followed by transfer to nitrocellulose membrane and probing with anti-PrP specific monoclonal antibodies 6D11 diluted 1:10,000. Data of this experiment are shown in FIG. 1. RAP significantly inhibited the generation of $PrP^{res}$ in mo-vCJD-SP/63 cells but had no effect on total PrP in either mo-vCJD-SP/63 or control SP/76 cells. Treatment of both cell lines with anti-LRP 2629 antibodies had no visible effect on amount of total PrP or $PrP^{res}$ in mo-vCJD-SP/63 cells and $PrP^{c}$ in control SP/76 cells. On further propagation of up to three passages, recovered generation of $PrP^{res}$ in mo-vCJD-SP/63 cells treated with RAP to the levels similar to cells which were treated with antibodies or left untreated was observed.

Experiment 2

Next, a "time-course" experiment was performed to examine when the inhibition of $PrP^{res}$ generation occurred after the treatment of cells with 1 μM RAP.

Cells of mo-vCJD-SP/63 cell line were plated into 6 cm Petri dishes ~3 hrs prior experiment at ~50% confluent density and were incubated at 37° C. in presence of 5% $CO_2$ to allow cell adhesion. Next, 1 μM RAP was added and cell cultures were maintained at 37° C. in presence of 5% $CO_2$. Cells were collected after 15 min, 30 min, 1, 2, 8, 12 and 24 hrs and processed for western blotting using the procedures described in Experiment 1. Data from this experiment are shown in FIG. 2.

The western blot shows significant inhibition of $PrP^{res}$ generation in cells collected 24 hours following exposure to RAP.

Experiment 3

In our previous experiments, a 1 μM concentration of RAP was used. In this experiment, the effect of lower and higher concentrations of RAP on $PrP^{res}$ formation and the minimal inhibiting concentration of RAP were determined.

Cells of mo-vCJD-SP/63 cell line were plated into 6 cm Petri dishes ~3 hrs prior experiment at ~50% confluent density and were maintained at 37° C. in presence of 5% $CO_2$ to allow cell adhesion. Next, RAP at various concentrations, 50 nM, 250 nM, 500 nM, 750 nM, 1 μM, 1.5 μM and 2 μM, was added to the plates and cell cultures were maintained at 37° C. in presence of 5% $CO_2$. Cells were collected after 24 hrs and processed using the procedures described in Experiment 1. Data from this experiment are shown in FIG. 3.

RAP profoundly inhibited the generation of $PrP^{res}$ when used at 250 nM concentration. Increasing concentrations up to 2 μM produced no further inhibiting effect. No inhibitory effect was observed when RAP was used at concentrations of 50 nM and below.

Experiment 4

In this experiment the inhibitory effect of 500 nM RAP was tested in two cell culture persistently infected either with mo-vCJD (mo-vCJD-SP/63) or Fukuoka-1 agent (Fu-SP/58).

Cells of either mo-vCID-SP/63 or Fu-SP/58 cell lines were plated into 6 cm Petri dishes ~1 hrs prior experiment at ~50% confluent density for each cell line and were maintained at 37° C. in presence of 5% $CO_2$ to allow cell adhesion. One hour later the medium was exchanged for either BM or BLGM medium and RAP was added to each cell culture to rich final concentration of 500 nM. Cell cultures were maintained at 37° C. in presence of 5% $CO_2$. Cells were collected after 24 hrs and processed using the procedures described in Experiment 1. Data from this experiment are shown in FIG. 4.

RAP significantly inhibited the generation of $PrP^{res}$ under tested conditions in mo-vCJD-SP/63 and in Fu-SP/58 cell cultures.

Experiment 5

A "time-course" experiment was repeated to examine when the inhibition of $PrP^{res}$ generation occurred after the treatment with r 500 nM of RAP Cells of mo-vCJD-SP/63 cell line were plated into 6 cm Petri dishes ~1 hrs prior experiment at ~50% confluent density and were incubated at 37° C. in presence of 5% $CO_2$ to allow cell adhesion. Next, either 500 nM RAP was added to the cell cultures or cell cultures were left untreated. Cell cultures were maintained at 37° C. in presence of 5% $CO_2$. Cells were collected after 4, 8, 12 and 24 hrs and processed for western blotting using the procedures described in Experiment 1. Data from this experiment are shown in FIG. 5.

Once again, RAP inhibited $PrP^{res}$ formation in a timely manner with significant inhibition observed 12 hours following treatment. Cells that were left untreated with RAP generated $PrP^{res}$ during the 24 hours with slightly increased amounts after 12 hours.

Experiment 6

The inhibitory effect of 500 nM RAP was tested in bone marrow-derived cell culture 336-2BMS-Fu2 persistently propagating Fu agent.

Cells of 336-2BMSFu2 cell line were plated into 25 $cm^2$ flasks ~1 hrs prior experiment at ~25% confluent density for each cell line and were maintained at 37° C. in presence of 5% $CO_2$ to allow cell adhesion. After one hour the medium was exchanged for a fresh one and 500 nM RAP (final concentration) was added to the cell culture or cell cultures was left untreated (control). Cell cultures were maintained at 37° C. in presence of 5% $CO_2$. Cells were collected after 24 hrs and were processed using the procedures described in Experiment 1. Data from this experiment are shown in FIG. 6.

RAP significantly inhibited $PrP^{res}$ formation in 336-2BMS-Fu2 cell culture (lane 4) as compared to untreated control (lane 2) but had no effect on the level of total PrP (compare lane 1 and 3).

Experiment 7

In this experiment the effect of multiple treatments with 250 nM RAP on 336-2BMS-Fu2 cells was investigated. In addition the cell culture was further propagated to establish whether the treatment of cells caused transient inhibition of PrP$^{res}$ formation or lead to stable inhibition or cured cells completely.

Cells of the 336-2BMS-Fu2 cell line were plated into 25 cm$^2$ flasks ~1 hrs prior experiment at ~10% confluent density for each cell line and were maintained at 37° C. in presence of 5% CO$_2$ to allow cell adhesion. After one hour the medium was exchanged for a fresh one and 250 nM RAP (final concentration) was added to the cell culture or cell cultures was left untreated (control). The treatment of cells continued and 250 nM RAP was added after 8, 12, 12, 12, 12, 12 hours (total six treatments). Control cells were treated with medium only. During the experiment cell cultures were maintained at 37° C. in presence of 5% CO$_2$. Cells were collected after 12 hrs following the last treatment and portion of cells was used for further propagation and portion was processed for detection of PrP$^{res}$ Western blotting using the procedures described in Experiment 1. Cells were propagated through 20 passages with splitting of cells every 3-4 days and at each passage portion of cells was collected and processed for detection of PrP$^{res}$ Western blotting. Data from this experiment are shown in FIG. 7.

Multiple treatments of cells with 250 nM RAP inhibited formation of PrP$^{res}$ as shown by the absence of the signal in lysates collected at 68 hours following initial treatment. During further propagation through 20 passages the untreated cell culture continue to propagate PrP$^{res}$ while RAP-treated bone-marrow derived 336-2-BM-Fu2 cell culture infected with Fukuoka agent produced significantly lower, if any, PrP$^{res}$. The amount of total PrP was comparable in both RAP-treated and untreated cell cultures during the experiment.

The foregoing experiments demonstrate that RAP has a significant inhibitory effect in vitro on the generation of PrPd in murine spleen- and bone-marrow-derived stromal cell cultures persistently infected with either mouse-adapted vCJD or Fukuoka-1 agents. Data from experiment 7 show that continuous treatment with RAP has a long-term (up to 70 days) inhibitory effect on PrP$^{res}$ in infected cells. This shows that RAP, either directly or through interaction with other protein(s), is involved in inhibiting the formation of, and/or promoting the clearance of, PrP$^{res}$.

Experiment 8

To evaluate effect of RAP on TSE agent propagation in vivo we performed the following experiment.

Brain tissue from a sporadic CJD case was homogenized and serially diluted 10-fold from $10^{-3}$ to $10^{-6}$ suspension in PBS. Part of the volume of the samples was left untreated (Sample 1) and part was treated with 2 μM RAP (Sample 2). Groups of homozygous transgenic mice carrying human prion protein gene with methionine at position 129 were created: Mice in Groups 1 and 3, 4 and 6, 7 and 9, 10 received single intracranial injections of serially diluted ($10^{-3}$, $10^{-4}$, $10^{-5}$ and $10^{-6}$, respectively) Sample 1 in volume of 30 μl. Mice in Groups 2, 5, 8 and 11 received single intracranial injections of serially diluted ($10^{-3}$, $10^{-4}$, $10^{-5}$ and $10^{-6}$, respectively) Sample 2 in volume of 30 μl. To evaluate the therapeutic effect of RAP on development of the disease, mice from Groups 3, 6 and 9 received intracranial injections of 2 μM RAP in volume of 30 μl at 100 days following the injection of the infectious agent (Sample 1).

Summary of the experiment is provided in Table 1. At high concentration of the brain inoculum ($10^{-3}$) for infecting mice, RAP showed no effect on their survival when added to the brain homogenate immediately before the injection to prevent the infection (Group 2) or when used as a single dose treatment at 100 days following the injection of the infectious agent (Group 3). However, all mice in Groups 1, injected with brain homogenate, and in Group 2, injected with brain homogenate that was treated with RAP immediately before inoculation, died as result of infection as confirmed by the presence of PrP$^{res}$ in their brains while only four animals out of five from Group 3, that were treated intracranially with RAP at 100 days, died as a result of infection (one animal was tested negative for PrP$^{res}$ by western blotting). At lower dilution of brain homogenate ($10^{-4}$) for infecting mice we again observed differences in survival of mice untreated and treated with RAP. While all five mice died from infection in untreated by RAP Group 4 only four animals died as a result of infection in Group 5 and Group 6. One dead animal from Group 5 was tested negative for PrP$^{res}$ by Western blotting and one animal from Group 6 is still alive for more than 300 days following inoculation. The same trend was observed for infection while using even lower ($10^{-5}$) concentration of brain homogenate: as a result of infection three mice out of five died in Group 7, two mice out of five died in Group 8 and all three mice died in Group 9. We also observed statistically significant prolongation in the incubation period between Groups 4 and 6 (p=0.004) and 5 and 6 (p=0.001) while using t-test (SigmaPlot 8). However it seems that addition of RAP to the brain homogenate immediately before injecting the sample into mice shortened the incubation period (comparison between Groups 4 and 5, p=0.036). Differences in incubation periods were not statistically significant between Groups 7, 8 and 9 due to high variation which is generally observed for higher dilutions of the infectious agent. This phenomenon may obfuscate the significance of the RAP effect while tested on small size groups of mice. To address this, the larger groups of animals should be used.

RAP showed therapeutic effect on progression of TSE when administered to mice that received lower concentrations of the TSE agent.

TABLE 1

Effect of RAP on development of TSE in transgenic mice injected intracranially with sporadic CJD agent

| Groups | Dilution of the brain | Number of dead/alive/ inoculated animals | Number of animals tested (pos/neg) by WB | Incubation period (average ± SD) |
|---|---|---|---|---|
| 1 | $10^{-3}$ (Sample 1) | 5/0/5 | 5/0 | 173.2 ± 5.8 |
| 2 | $10^{-3}$ + RAP (Sample 2) | 5/0/5 | 5/0 | 164.6 ± 9.8 |
| 3 | $10^{-3}$ (Sample 1) + RAP 100 day | 5/0/5 | 4/1 | 179.5 ± 18.5 |
| 4 | $10^{-4}$ (Sample 1) | 5/0/5 | 5/0 | 193 ± 5.6 |

TABLE 1-continued

Effect of RAP on development of TSE in transgenic mice injected intracranially with sporadic CJD agent

| Groups | Dilution of the brain | Number of dead/alive/ inoculated animals | Number of animals tested (pos/neg) by WB | Incubation period (average ± SD) |
|---|---|---|---|---|
| 5 | $10^{-4}$ + RAP (Sample 2) | 5/0/5 | 5/1 | 185 ± 1.4 |
| 6 | $10^{-4}$ (Sample 1) + RAP 100 day | 4/1/5 | 4/0 | 215.3 ± 11.4 |
| 7 | $10^{-5}$ (Sample 1) | 4/1/5 | 4/0 | 246 ± 47 |
| 8 | $10^{-5}$ + RAP (Sample 2) | 2/3/5 | 2/0 | 245 ± 58 |
| 9 | $10^{-5}$ (Sample 1) + RAP 100 day | 3/0/3 | 3/0 | 240.3 ± 20.5 |
| 10 | $10^{-6}$ | 0/5/5 | n.a. | 345 days |
| 11 | $10^{-6}$ + RAP | 0/5/5 | n.a. | 345 days |

Statistical analysis was performed using t-test (SigmaPlot 8).
Statistically significant differences were found when comparing Groups 4 and 5 (p = 0.03), 4 and 6 (p = 0.006) and 5 and 6 (p = 0.002)

The findings disclosed herein suggest that RAP will be effective in the treatment, and prophylaxis, of other protein misfolding diseases. Exemplary of such diseases are those of Table 2, below.

TABLE 2

Other Protein Misfolding Diseases In Which RAP Is Likely To Have Therapeutic Effect

| Protein | Disease |
|---|---|
| Amylin | Type II Diabetes |
| $\alpha_{1A}$-voltage-dependent calcium channel subunit | Spinocerebral ataxia type 6 |
| ABri | Familial British dementia |
| α-Galactosidase A | Fabry's disease |
| Androgen receptor | Spinobulbular muscular atrophy |
| α-Synuclein | Parkinson's disease |
| Ataxins | Ataxia |
| ATP7B | Wilson disease |
| Atrial natriuretic factor | Atrial amyloidosis of heart |
| Atrophin | Dentatorubral pallidoluysian atrophy |
| $\beta_2$-Microglobulin | Haemodialysis-associated amyloidosis |
| β-Amyloid | Alzheimer's disease |
| β-Amyloid | Hereditary cerebral amyloid angiopathy |
| β-Glucocerebrosidase | Gaucher's disease |
| Calcitonin | Medullary carcinoma of thyroid |
| Cystatin C | Hereditary cerebral amyloid angiopathy |
| Cystic fibrosis transmembrane regulator protein | Cystic fibrosis |
| Fibrillin | Marfan syndrome |

TABLE 2-continued

Other Protein Misfolding Diseases In Which RAP Is Likely To Have Therapeutic Effect

| Protein | Disease |
|---|---|
| Fragile X mental retardation-1 protein | Fragile X syndrome |
| Fragile X mental retardation-2 protein | Fragile XE syndrome |
| Gelsolin | Finnish type famillial amyloidosis |
| Glial fibrillary acidic protein (GFAP) | Alexander disease |
| Gonadotropin-release hormone receptor | Huntington's disease |
| Huntingtin | Huntington's disease |
| Ig $V_L$ domain | Light chain amyloidosis |
| Lysozyme | Fatal systemic amyloidosis |
| Machado-Joseph disease protein 1 | Machado-Joseph disease |
| Medin | Hereditary systemic amyloidosis |
| Myotonic dystrophy protein kinase | Myotonic dystrophy |
| Nephrogenic diabetes isipidus | Aquaporin-Vasopressin-1 |
| p53 | Cancer |
| Prion proteins | Prion diseases |
| Rhodopsin | Retinitis pigmentosa protein |
| Serum amyloid A (SAA) | Secondary systemic amyloidosis |
| Superoxide dismutase | Amyotrophic lateral sclerosis |
| Tau | Alzheimer's disease |
| Tau | Frontotemporal dementia |
| Transthyretin | Famillial amyloid polyneuropathy |
| von Hippel Lindau protein | Cancer |

What is claimed is:

1. A method of delaying the progression of a prion disease in a subject, comprising administering to the subject an effective amount of a RAP agent.

2. The method of claim 1, wherein the prion disease is selected from the group consisting of various forms of Creutzfeldt-Jakob disease (CJD), iatrogenic Creutzfeldt-Jakob disease (iCJD), variant Creutzfeldt-Jakob disease (vCJD), familial Creutzfeldt-Jakob disease (fCJD), sporadic Creutzfeldt-Jakob disease (sCJD); Gerstmann-Straussler-Scheinker syndrome (GSS); Fatal insomnia, familial (FFI) or sporadic, Kuru; Scrapie; Bovine spongiform encephalopathy (BSE); Transmissible mink encephalopathy (TME); Chronic wasting disease (CWD); Feline spongiform encephalopathy; and Exotic ungulate encephalopathy (EUE).

3. The method of claim 1, wherein the subject is a mammal selected from the group consisting of human, sheep, goat, cow, mink, white-tailed deer, elk, mule deer, moose, cat, nyala, gemsbok, oryx, eland, kudu, ankole, and bison.

4. The method of claim 1, wherein the subject is a human.

5. The method of claim 1, wherein the RAP agent is a RAP polypeptide selected from the group consisting of:
   (a) a polypeptide comprising amino acids 35-357 of SEQ ID NO: 1;
   (b) a polypeptide comprising an amino acid sequence having 90% to 100% sequence identity to amino acids 35-357 of SEQ ID NO: 1;
   (c) a polypeptide comprising an amino acid sequence of SEQ ID NO: 2, SEQ ID NO: 3, SEQ ID NO: 4, SEQ ID NO: 5, SEQ ID NO: 6, or SEQ ID NO: 7; and
   (d) combinations thereof.

6. The method of claim 5, wherein the RAP polypeptide comprises amino acids 35-357 of SEQ ID NO; 1.

7. The method of claim 1, rein the mode of administration is intranasal.

8. The method of claim 7, wherein the RAP agent is compounded with an aqueous vehicle prior to administration to the subject.

9. The method of claim 1, wherein the RAP agent is administered to achieve in vivo plasma concentration of the agent of 0.01 ng/cc to 10,000 ng; cc.

10. The method of claim 1, wherein the RAP agent is administered to achieve in vivo plasma concentration of the agent of 0.01 ng/cc to 1,000 ng/cc.

11. The method of claim 1, wherein the RAP agent is administered to the subject at a dose of 0.01 to 100 mg/kg body weight/day.

12. The method of claim 1, wherein the RAP agent is administered to the subject at a dose of 30 mg/kg body weight/day.

* * * * *

UNITED STATES PATENT AND TRADEMARK OFFICE
CERTIFICATE OF CORRECTION

PATENT NO. : 9,051,390 B2
APPLICATION NO. : 13/265242
DATED : June 9, 2015
INVENTOR(S) : Larisa Cervenakova et al.

It is certified that error appears in the above-identified patent and that said Letters Patent is hereby corrected as shown below:

In the drawings

In FIG. 1, Sheet 1 of 9, in the title, delete "PrPress" and insert -- $PrP^{res}$ --, therefor.

In FIG. 1, Sheet 1 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

In FIG. 1, Sheet 1 of 9, at bullet 5, delete "arrows" and insert -- arrow --, therefor.

In FIG. 2, Sheet 2 of 9, in the title, delete "Effect of 1 μMRAP on PrPres formation in mo-vCJD-SP/63 cell line infected with mouse-vCJD: Time-course," and insert -- Effect of 1 μM RAP on $PrP^{res}$ formation in mo-vCJD-SP/63 cell line infected with mouse-adapted vCJD: Time-course --, therefor.

In FIG. 2, Sheet 2 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

In FIG. 2, Sheet 2 of 9, at bullet 5, delete "arrows" and insert -- arrow --, therefor.

In FIG. 3, Sheet 7 of 9, in the title, delete "Effect of RAP on PrPres formation in mo-vCJD-SP/63 cell line infected with mouse-vCJD: Dose-dependent inhibition," and insert -- Effect of RAP on $PrP^{res}$ formation in mo-vCJD-SP/63 cell line infected with mouse-adapted vCJD: Dose-dependent inhibition --, therefor.

In FIG. 3, Sheet 7 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

Signed and Sealed this
Second Day of February, 2016

Michelle K. Lee
*Director of the United States Patent and Trademark Office*

CERTIFICATE OF CORRECTION (continued)
U.S. Pat. No. 9,051,390 B2

In the drawings

In FIG. 4, Sheet 4 of 9, in the title, delete "PrPress" and insert -- $PrP^{res}$ --, therefor.

In FIG. 4, Sheet 4 of 9, at bullet 1, delete "wither" and insert -- either --, therefor.

In FIG. 4, Sheet 4 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

In FIG. 5, Sheet 5 of 9, in the title, delete "PrPres" and insert -- $PrP^{res}$ --, therefor.

In FIG. 5, Sheet 5 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

In FIG. 6, Sheet 6 of 9, in the title, delete "PrPres" and insert -- $PrP^{res}$ --, therefor.

In FIG. 6, Sheet 6 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

In FIG. 6, Sheet 6 of 9, at bullet 5, delete "arrows" and insert -- arrow --, therefor.

In FIG. 7, Sheet 7 of 9, in the title, delete "PrPres" and insert -- $PrP^{res}$ --, therefor.

In FIG. 7, Sheet 7 of 9, at bullet 3, delete "(–) and (+) Proteinase K (PK)- treated samples represent total PrP and pathologic PrPress," and insert -- (–) and (+) Proteinase K (PK)- untreated and -treated samples represent total PrP and $PrP^{res}$ --, therefor.

UNITED STATES PATENT AND TRADEMARK OFFICE
CERTIFICATE OF CORRECTION

| | | |
|---|---|---|
| PATENT NO. | : 9,051,390 B2 | Page 1 of 1 |
| APPLICATION NO. | : 13/265242 | |
| DATED | : June 9, 2015 | |
| INVENTOR(S) | : Larisa Cervenakova et al. | |

It is certified that error appears in the above-identified patent and that said Letters Patent is hereby corrected as shown below:

In the claims

At Column 32, line 17, in claim 7, "rein the mode of administration" should read -- wherein the mode of administration --

At Column 32, line 25, in claim 9, "10,000 ng;cc" should read -- 10,000 ng/cc --

Signed and Sealed this
Ninth Day of August, 2016

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 357
<212> TYPE: PRT
<213> ORGANISM: Homo sapiens

<400> SEQUENCE: 1

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45
```

```
Glu Ser Gly Glu Glu Phe Arg Met Glu Lys Leu Asn Gln Leu Trp Glu
     50                  55                  60

Lys Ala Gln Arg Leu His Leu Pro Pro Val Arg Leu Ala Glu Leu His
 65                  70                  75                  80

Ala Asp Leu Lys Ile Gln Glu Arg Asp Glu Leu Ala Trp Lys Lys Leu
                 85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
            115                 120                 125

Asp Ala Arg Gln Val Thr Ser Asn Ser Leu Ser Gly Thr Gln Glu Asp
130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
            195                 200                 205

Leu Ser Asp Ile Lys Gly Ser Val Leu His Ser Arg His Thr Glu Leu
210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Leu Lys His Phe Glu Ala Lys Ile
            275                 280                 285

Glu Lys His Asn His Tyr Gln Lys Gln Leu Glu Ile Ala His Glu Lys
            290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
            355

<210> SEQ ID NO 2
<211> LENGTH: 323
<212> TYPE: PRT
<213> ORGANISM: Xenopus laevis

<400> SEQUENCE: 2

Tyr Ser Arg Glu Lys Asn Gln Pro Glu Pro Pro Lys Arg Glu Ser
 1               5                  10                  15

Gly Glu Glu Phe Arg Met Glu Lys Leu Asn Gln Leu Trp Glu Lys Ala
                 20                  25                  30

Gln Arg Leu His Leu Pro Pro Val Arg Leu Ala Glu Leu His Ala Asp
             35                  40                  45

Leu Lys Ile Gln Glu Arg Asp Glu Leu Ala Trp Lys Lys Leu Lys Leu
 50                  55                  60
```

```
Asp Gly Leu Asp Glu Asp Gly Lys Glu Ala Arg Leu Ile Arg Asn
65                  70                  75                  80

Leu Asn Val Ile Ser Ala Lys Tyr Gly Leu Asp Gly Lys Lys Asp Ala
            85                  90                  95

Arg Gln Val Thr Ser Asn Ser Leu Ser Gly Thr Gln Gly Asp Gly Leu
            100                 105                 110

Asp Asp Pro Arg Leu Glu Lys Leu Trp His Lys Ala Lys Thr Ser Gly
            115                 120                 125

Lys Phe Ser Ser Glu Glu Leu Asp Lys Leu Trp Arg Glu Phe Leu His
130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Asn Val Leu His Ser Arg His Thr Glu Leu Lys Glu
            180                 185                 190

Lys Leu Arg Ser Ile Asn Gln Gly Leu Asp Arg Leu Arg Arg Val Ser
            195                 200                 205

His Gln Gly Tyr Ser Thr Glu Ala Glu Phe Glu Glu Pro Arg Val Ile
210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
            275                 280                 285

Lys His Ala Leu Leu Glu Gly Arg Thr Lys Glu Leu Gly Tyr Thr Val
            290                 295                 300

Lys Lys His Leu Gln Asp Leu Ser Ser Arg Ile Ser Arg Ala Arg His
305                 310                 315                 320

Asn Glu Leu

<210> SEQ ID NO 3
<211> LENGTH: 323
<212> TYPE: PRT
<213> ORGANISM: Danio rerio

<400> SEQUENCE: 3

Tyr Ser Arg Glu Lys Asn Glu Pro Glu Met Ala Ala Lys Arg Glu Ser
1               5                   10                  15

Gly Glu Glu Phe Arg Met Glu Lys Leu Asn Gln Leu Trp Glu Lys Ala
            20                  25                  30

Lys Arg Leu His Leu Ser Pro Val Arg Leu Ala Glu Leu His Ser Asp
        35                  40                  45

Leu Lys Ile Gln Glu Arg Asp Glu Leu Asn Trp Lys Lys Leu Lys Val
    50                  55                  60

Glu Gly Leu Asp Lys Asp Gly Lys Glu Ala Lys Leu Ile His Asn
65                  70                  75                  80

Leu Asn Val Ile Leu Ala Arg Tyr Gly Leu Asp Gly Arg Lys Asp Ala
            85                  90                  95

Gln Met Val His Ser Asn Ala Leu Asn Glu Asp Thr Gln Asp Glu Leu
            100                 105                 110
```

-continued

Gly Asp Pro Arg Leu Glu Lys Leu Trp His Lys Ala Lys Thr Ser Gly
            115                 120                 125

Lys Phe Ser Ser Glu Glu Leu Asp Lys Leu Trp Arg Glu Phe Leu His
    130                 135                 140

Tyr Lys Glu Lys Ile Gln Glu Tyr Asn Val Leu Leu Asp Thr Leu Ser
145                 150                 155                 160

Arg Ala Glu Glu Gly Tyr Glu Asn Leu Leu Ser Pro Ser Asp Met Ala
                165                 170                 175

His Ile Lys Ser Asp Thr Leu Ile Ser Lys His Ser Glu Leu Lys Asp
            180                 185                 190

Arg Leu Arg Ser Ile Asn Gln Gly Leu Asp Arg Leu Arg Lys Val Ser
        195                 200                 205

His Gln Gly Tyr Gly Ser Thr Thr Glu Phe Glu Glu Pro Arg Val Ile
    210                 215                 220

Asp Leu Trp Asp Leu Ala Gln Ser Ala Asn Phe Thr Glu Lys Glu Leu
225                 230                 235                 240

Glu Ser Phe Arg Glu Glu Leu Lys His Phe Glu Ala Lys Ile Glu Lys
                245                 250                 255

His Asn His Tyr Gln Lys Gln Leu Glu Ile Ser His Gln Lys Leu Lys
            260                 265                 270

His Val Glu Ser Ile Gly Asp Pro Glu His Ile Ser Arg Asn Lys Glu
        275                 280                 285

Lys Tyr Val Leu Leu Glu Lys Thr Lys Glu Leu Gly Tyr Lys Val
    290                 295                 300

Lys Lys His Leu Gln Asp Leu Ser Ser Arg Val Ser Arg Ala Arg His
305                 310                 315                 320

Asn Glu Leu

<210> SEQ ID NO 4
<211> LENGTH: 323
<212> TYPE: PRT
<213> ORGANISM: Pongo abeli

<400> SEQUENCE: 4

Tyr Ser Arg Glu Lys Asn Glu Pro Glu Met Ala Ala Lys Arg Glu Ser
1               5                   10                  15

Gly Glu Glu Phe Arg Met Glu Lys Leu Asn Gln Leu Trp Glu Lys Ala
            20                  25                  30

Lys Arg Leu His Leu Ser Pro Val Arg Leu Ala Glu Leu His Ser Asp
        35                  40                  45

Leu Lys Ile Gln Glu Arg Asp Glu Leu Asn Trp Lys Lys Leu Lys Val
    50                  55                  60

Glu Gly Leu Asp Gly Asp Gly Glu Lys Glu Ala Lys Leu Val His Asn
65                  70                  75                  80

Leu Asn Val Ile Leu Ala Arg Tyr Gly Leu Asp Gly Arg Lys Asp Thr
                85                  90                  95

Gln Thr Val His Ser Asn Ala Leu Asn Glu Asp Thr Gln Asp Glu Leu
            100                 105                 110

Gly Asp Pro Arg Leu Glu Lys Leu Trp His Lys Ala Lys Thr Ser Gly
        115                 120                 125

Lys Phe Ser Ser Glu Glu Leu Asp Lys Leu Trp Arg Glu Phe Leu His
    130                 135                 140

Tyr Lys Glu Lys Ile His Glu Tyr Asn Val Leu Leu Asp Thr Leu Ser
145                 150                 155                 160

Arg Ala Glu Glu Gly Tyr Glu Asn Leu Leu Ser Pro Ser Asp Met Thr
            165                 170                 175

His Ile Lys Ser Asp Thr Leu Ala Ser Lys His Ser Glu Leu Lys Asp
            180                 185                 190

Arg Leu Arg Ser Ile Asn Gln Gly Leu Asp Arg Leu Arg Lys Val Ser
            195                 200                 205

His Gln Gly Tyr Gly Pro Ala Thr Glu Phe Glu Glu Pro Arg Val Ile
            210                 215                 220

Asp Leu Trp Asp Leu Ala Gln Ser Ala Asn Phe Thr Glu Lys Glu Leu
225                 230                 235                 240

Glu Ser Phe Arg Glu Glu Leu Lys His Phe Glu Ala Lys Ile Glu Lys
            245                 250                 255

His Asn His Tyr Gln Lys Gln Leu Glu Ile Ser His Gln Lys Leu Lys
            260                 265                 270

His Val Glu Ser Ile Gly Asp Pro Glu His Ile Ser Arg Asn Lys Glu
            275                 280                 285

Lys Tyr Val Leu Leu Glu Glu Lys Thr Lys Glu Leu Gly Tyr Lys Val
            290                 295                 300

Lys Lys His Leu Gln Asp Leu Ser Ser Arg Val Ser Arg Ala Arg His
305                 310                 315                 320

Asn Glu Leu

<210> SEQ ID NO 5
<211> LENGTH: 325
<212> TYPE: PRT
<213> ORGANISM: Mus musculus

<400> SEQUENCE: 5

Tyr Thr Arg Glu Ala Asn Glu Gly Leu Ala Asp Ala Lys Arg Arg Glu
1               5                   10                  15

Ala Gly Glu Phe Arg Val Val Arg Leu Asn Gln Val Trp Glu Lys Ala
            20                  25                  30

Gln Arg Leu Gln Leu Ser Ala Val Lys Leu Ala Glu Leu His Ser Asp
            35                  40                  45

Leu Lys Ile Gln Glu Lys Asp Glu Leu Ser Trp Lys Lys Leu Lys Ala
        50                  55                  60

Glu Gly Leu Gly Glu Asp Gly Lys Glu Ala Lys Leu Arg Arg Asn
65                  70                  75                  80

Ile Asn Val Ile Met Thr Lys Tyr Gly Met Asn Gly Lys Lys Asp Ser
            85                  90                  95

His Leu Thr Asp Thr Asn Tyr Ile Lys Asp Gly Thr Glu Ser Asp Thr
            100                 105                 110

Leu Asp Asp Pro Arg Leu Glu Lys Leu Trp Ser Lys Ala Lys Thr Ser
            115                 120                 125

Gly Lys Phe Ser Asp Glu Glu Leu Asp Lys Leu Trp Arg Glu Phe Lys
            130                 135                 140

His His Lys Glu Lys Ile Arg Glu Tyr Asn Ile Leu Leu Glu Thr Val
145                 150                 155                 160

Ser Arg Thr Glu Asp Ile His Lys Lys Val Ile Asn Pro Ser Glu Glu
            165                 170                 175

Asn Pro Val Lys Glu Glu Val Leu His Asn Lys His Arg Glu Leu Lys
            180                 185                 190

Glu Lys Leu Arg Ser Ile Asn Gln Gly Phe Glu Arg Leu Arg Lys Val
            195                 200                 205

Ser His Gln Gly Tyr Asp Ala Thr Ser Glu Phe Glu Glu Pro Arg Val
210                 215                 220

Ile Asp Leu Trp Asp Met Ala Lys Ser Ala Asn Phe Thr Glu Lys Glu
225                 230                 235                 240

Leu Glu Ser Phe Arg Glu Leu Lys His Phe Glu Ala Lys Ile Glu
            245                 250                 255

Lys His His His Tyr Gln Lys Gln Leu Glu Ile Ser His Glu Lys Leu
            260                 265                 270

Lys His Ile Glu Gly Thr Gly Asp Lys Glu His Leu Asn Arg Asn Arg
        275                 280                 285

Glu Lys Tyr Ala Met Leu Glu Glu Lys Thr Lys Glu Leu Gly Tyr Lys
        290                 295                 300

Val Lys Lys His Leu Gln Asp Leu Ser Ser Arg Ile Ser Gln Gly Leu
305                 310                 315                 320

Gln His Asn Glu Leu
            325

<210> SEQ ID NO 6
<211> LENGTH: 323
<212> TYPE: PRT
<213> ORGANISM: Rattus norvegicus

<400> SEQUENCE: 6

Tyr Ser Arg Asp Val Asn Glu Asn His Ser Glu Arg Asp Ser Ala Val
1               5                   10                  15

Glu Phe Arg Ile Met Arg Leu Asn Gln Ile Trp Glu Lys Ala Gln Arg
            20                  25                  30

Leu Gln Leu Ser Ser Val Gln Leu Thr Glu Leu His Ser Asp Leu Lys
        35                  40                  45

Ile Gln Glu Lys Asp Glu Leu Asn Trp Lys Lys Leu Lys Val Asp Gly
    50                  55                  60

Leu Asp Asp Asp Gly Glu Lys Glu Ala Lys Leu Arg Arg Ser Leu Asn
65                  70                  75                  80

Val Ile Leu Thr Lys Tyr Gly Leu Asp Gly Lys Lys Lys Thr Gln Thr
                85                  90                  95

Glu Asp Ser Asn Phe Ile Lys Asp Ser Lys Glu Asn Asp Ile Leu Asn
            100                 105                 110

Asp Pro Arg Leu Glu Lys Leu Trp Asn Lys Ala Lys Thr Ser Ala Thr
        115                 120                 125

Phe Ser Glu Glu Glu Leu Glu Ser Leu Trp Arg Glu Phe Val His His
    130                 135                 140

Lys Glu Lys Ile Ser Glu Tyr Asn Ile Leu Leu Asp Thr Val Ser Arg
145                 150                 155                 160

Thr Glu Glu Ile His Lys Asn Val Ile Ser Pro Asp Glu His Glu Ile
                165                 170                 175

Lys Glu Asp Ile Leu His Ala Lys His Thr Asp Leu Lys Glu Arg Leu
            180                 185                 190

Arg Ser Ile Asn Gln Gly Tyr Glu Arg Leu Arg Lys Leu Ser His Glu
        195                 200                 205

Gly Tyr Ile Thr Ala Arg Glu Phe Asn Glu Pro Arg Val Asn Asp Leu
    210                 215                 220

Trp Asp Met Ala Lys Asp Ala Asn Phe Ser Asp Ser Glu Leu Glu Ser
225                 230                 235                 240

Phe Lys Glu Glu Leu Lys His Phe Glu Thr Lys Ile Glu Lys His Gln

```
                 245                 250                 255
His Tyr Gln Lys Gln Leu Glu Ile Ser His Gly Lys Leu Lys His Ile
                260                 265                 270

Ala Asp Thr Gly Asp Lys Glu His Leu Met Arg Ser Lys Glu Lys His
            275                 280                 285

Ser Met Leu Thr Glu Lys Ile Lys Glu Leu Gly Tyr Lys Val Lys Lys
    290                 295                 300

His Leu Gln Asp Leu Thr Ser Arg Ala Ser Arg Gly Gly Leu Gln His
305                 310                 315                 320

Asn Glu Leu

<210> SEQ ID NO 7
<211> LENGTH: 327
<212> TYPE: PRT
<213> ORGANISM: Gallus gallus

<400> SEQUENCE: 7

Tyr Ser Lys Glu Met Asn Glu Lys Asn Ala Ser Asp Lys Ser Asn Asn
1               5                   10                  15

Gln Val Glu Phe Arg Ile Ala Lys Leu Asn Gln Val Trp Glu Lys Ala
            20                  25                  30

Ile Arg Met Gln Leu Ala Pro Val Arg Leu Ser Glu Leu His Ser Asp
        35                  40                  45

Leu Lys Ile Gln Glu Lys Asp Glu Leu Gln Trp Lys Leu Lys Lys Ala
    50                  55                  60

Glu Gly Met Asp Glu Asp Gly Leu Arg Glu Ala Lys Leu Arg Arg Asn
65                  70                  75                  80

Phe Asn Ile Ile Leu Ala Lys Tyr Gly Met Asp Gly Lys Lys Asp Thr
                85                  90                  95

Arg Thr Leu Asp Ser Asn Arg Leu Lys Asp His Glu Val Lys Ile Gly
            100                 105                 110

Asp Thr Phe Asp Asp Pro Lys Leu Asp Lys Leu Trp Asn Lys Ala Arg
        115                 120                 125

Thr Ser Gly Lys Phe Ser Asp Glu Glu Leu Gln Thr Leu His Arg Glu
    130                 135                 140

Phe Gln His His Lys Asp Lys Ile His Glu Tyr Asn Ile Val Met Asp
145                 150                 155                 160

Thr Val Ser Arg Thr Glu Glu Ile His Lys Asn Val Ile Ser Pro Leu
                165                 170                 175

Glu Gly Asp Val Lys Glu Asn Val Leu His Gln Lys His Thr Asp Leu
            180                 185                 190

Lys Gln Arg Met Arg Asp Leu Asn Gln Gly Phe Glu Arg Leu Arg Lys
        195                 200                 205

Ile Thr His Glu Gly Tyr Thr Asp Asp Ser Glu Phe Arg Glu Pro Arg
    210                 215                 220

Val Ile Glu Leu Trp Glu Met Ala Lys Arg Ser Asn Leu Ser Glu Asp
225                 230                 235                 240

Glu Leu Asp Ser Leu Lys Glu Glu Leu Arg His Phe Glu Thr Lys Val
                245                 250                 255

Glu Lys His Gln His Tyr Gln Glu Gln Leu Glu Leu Ser His Gln Lys
            260                 265                 270

Leu Lys His Val Glu Ala Leu Gly Asp Glu Asp His Ile Met Arg Asn
        275                 280                 285

Lys Glu Lys Tyr Asn Thr Leu Ala Glu Lys Ala Arg Glu Met Gly Tyr
```

```
                    290                 295                 300
Lys Met Lys Lys His Leu Gln Asp Leu Thr Asn Lys Leu Ser Lys Asn
305                 310                 315                 320

Gly Leu Gln His Asn Glu Leu
                325
```